(12) United States Patent
Barker et al.

(10) Patent No.: US 12,070,414 B2
(45) Date of Patent: Aug. 27, 2024

(54) MEDICAL TOOLS FOR CORNEAL TISSUE DELIVERY

(71) Applicant: CORNEAGEN, Seattle, WA (US)

(72) Inventors: Jerry W. Barker, Gretna, VA (US); Kevin Potts, Lexington, NC (US)

(73) Assignee: CorneaGen, Seattle, WA (US)

( * ) Notice: Subject to any disclaimer, the term of this patent is extended or adjusted under 35 U.S.C. 154(b) by 319 days.

(21) Appl. No.: 17/375,279

(22) Filed: Jul. 14, 2021

(65) Prior Publication Data

US 2022/0015944 A1  Jan. 20, 2022

Related U.S. Application Data

(60) Provisional application No. 63/052,957, filed on Jul. 17, 2020.

(51) Int. Cl.
*A61F 9/00* (2006.01)
*A61F 9/013* (2006.01)

(52) U.S. Cl.
CPC ............ *A61F 9/0017* (2013.01); *A61F 9/013* (2013.01)

(58) Field of Classification Search
CPC ...... A61F 9/0017; A61F 9/013; A61F 2/1678; A61F 2/0095
See application file for complete search history.

(56) References Cited

U.S. PATENT DOCUMENTS

| | | | |
|---|---|---|---|
| 4,880,000 A | 11/1989 | Holmes et al. | |
| 6,543,610 B1 | 4/2003 | Nigam | |
| 9,549,848 B2 | 1/2017 | Schneider et al. | |
| 2014/0142587 A1* | 5/2014 | Walter | A61F 2/148 606/107 |
| 2017/0196681 A1* | 7/2017 | Berner | A61F 2/148 |
| 2019/0192282 A1* | 6/2019 | Walter | A61F 2/148 |
| 2020/0206029 A1 | 7/2020 | Abdullayev et al. | |

FOREIGN PATENT DOCUMENTS

EP  1981437 B1  5/2016

OTHER PUBLICATIONS

CorneaGen (Nov. 8, 2018). Corneagen endoserter. Vimeo, Nov. 8, 2018 (Oct. 14, 2018), https://vimeo.com/371941596. (Year: 2018).*
CorneaGen, "Corneagen endoserter" Vimeo, Nov. 8, 2018, https:vimeo.com/371941596, 4 pages.
International Search Report and Written Opinion, PCT/US2021/041557, mailed Oct. 27, 2021, 10 pages.
Jun. 21, 2024—EESR, EP Application No. 21841553.7.

\* cited by examiner

*Primary Examiner* — Ashley L Fishback
*Assistant Examiner* — Chima U Igboko
(74) *Attorney, Agent, or Firm* — POLSINELLI PC

(57) ABSTRACT

Devices, kits and tools that facilitate pre-loading, storage, transportation and small incision, partial thickness corneal replacement procedures, including deep lamellar endothelial keratoplasty (DLEK), Descemet's stripping endothelial keratoplasty (DSEK) and Descemet's stripping automated endothelial keratoplasty (DSAEK), using donor eye tissue are provided.

23 Claims, 18 Drawing Sheets

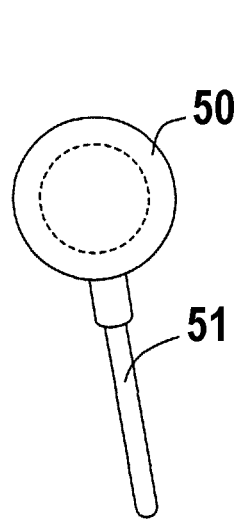
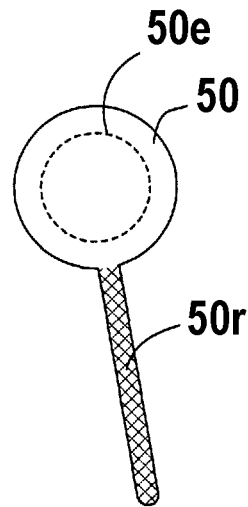
FIG. 15A  FIG. 15B
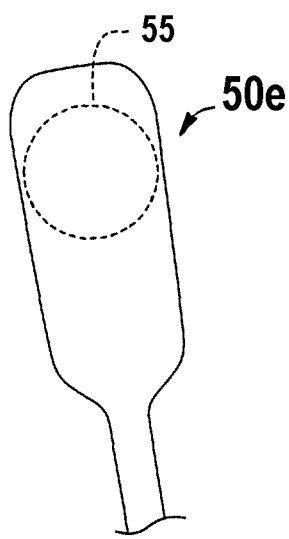
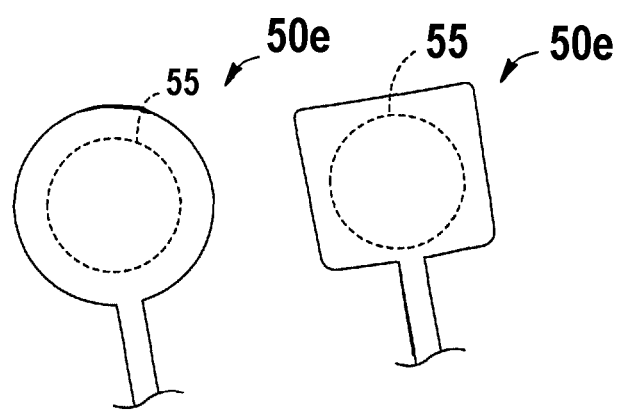
FIG. 16A  FIG. 16B  FIG. 16C

MEDICAL TOOLS FOR CORNEAL TISSUE DELIVERY

CROSS-REFERENCE TO RELATED APPLICATION

This application claims the benefit of priority to U.S. Provisional Patent Application No. 63/052,957, filed Jul. 17, 2020 which is incorporated by reference herein in its entirety.

FIELD

The present disclosure relates (i) pre-loading of processed donor eye tissue in an implant tool at a location (e.g., a tissue bank) apart from a patient surgery location, (ii) storage and transportation to a patient surgery location of the donor eye tissue loaded in the implant tool, and (iii) performance of small incision corneal transplantation surgery with the implant tool, where the loaded donor eye tissue is in a ready-to-transplant state.

BACKGROUND

Endothelial dysfunction is a leading cause of corneal vision loss and treatment requires surgical replacement with donor endothelium. Conventional corneal transplantation surgery, also known as penetrating keratoplasty, uses full-thickness corneal replacement with sutures and thus suffers from the inherent problems of surface corneal incisions and sutures and poor wound healing of vertical stromal wounds. More recently, other more advanced surgeries have supplanted penetrating keratoplasty, among them deep lamellar endothelial keratoplasty (DLEK), Descemet's stripping endothelial keratoplasty (DSEK) and Descemet's stripping automated endothelial keratoplasty (DSAEK). These techniques have been used to place a partial-thickness corneal replacement from a healthy donor cornea into a host/recipient along with its endothelium through a limbal scleral incision that leaves the surface of the recipient cornea untouched. These procedures are also known as "stitchless" corneal transplantation techniques.

DLEK was a major advance in the way that diseased human cornea is replaced with healthy donor corneal endothelium, but it was not universally accepted by corneal surgeons due to the demands in the surgical skillset to perform such a procedure on a routine basis. After simplification of the procedure with DSEK surgery, followed by donor tissue preparation automation provided by DSAEK, selective corneal transplantation became a reality for the first time and it was largely accepted by corneal surgeons worldwide.

In small incision procedures, the donor tissue (e.g., cornea) must be processed to make it suitable for transplantation. Outcomes can vary greatly depending on how well a practitioner can process the donor tissue. Additionally, time and expertise are required to prepare the recipient's eye for a donor tissue graft. The amount of time required for preparation can limit the number of procedures that a practitioner can perform.

SUMMARY

Embodiments of the present disclosure are directed to methods and apparatus that can facilitate: (i) pre-loading of processed donor eye tissue in an implant tool at a location (e.g., a tissue bank) apart from a patient surgery location, (ii) storage and transportation to a patient surgery location of the donor eye tissue loaded in the implant tool, and (iii) performance of small incision corneal transplantation surgery with the implant tool, where the loaded donor eye tissue is in a ready-to-transplant state. Such embodiments allow standardization of donor tissue processing at the location apart from a patient surgery location, whereby the outcomes can be enhanced.

One aspect of the present disclosure is directed to a donor corneal tissue storage and delivery device. In some embodiments, the device comprises a housing having a proximal and distal end, a cannula, a fluid channel connector, at least one fluid channel, a flexible support, a retractor shaft, one or more loading members, a removable reservoir, a deployment shaft, and one or more deployment members.

In some embodiments, the cannula, having a proximal end and a distal end, is disposed at a distal end of the housing. In some embodiments the fluid channel connector is disposed at a proximal end of the housing. In some embodiments, the at least one fluid channel comprises a proximal end and a distal end, and in some embodiments, the proximal end of the at least one fluid channel is coupled to the fluid channel connector and the distal end is disposed proximate to within the proximal end of the cannula. In some embodiments, the flexible support is configured to receive donor corneal tissue and retract into the cannula. In some embodiments, the retractor shaft is coupled to the flexible support, and in some embodiments, the one or more loading members are held by the housing, coupled to the retractor shaft and operable to retract both the retractor shaft and coupled flexible support. In some embodiments, the flexible support and donor corneal tissue disposed on the flexible support are retracted into the cannula, and in some embodiments the flexible support and donor corneal tissue adopt a rolled shape when retracted into the cannula.

In some embodiments the removable reservoir is in fluid communication with the fluid channel and configured to enclose the flexible support and cannula and to receive a volume of fluid for hydrating the donor corneal tissue received by the flexible support while the flexible support is retracted into the cannula. In some embodiments the deployment shaft is coupled to the cannula and configured to retract into the distal end of the housing. In some embodiments the one or more deployment members is coupled to the deployment shaft and operable to cause the deployment shaft to retract the cannula and to deliver the donor corneal tissue to an implantation site from the flexible support retracted into the cannula.

In some embodiments of the donor corneal tissue storage and delivery device the cannula tapers toward the distal end of the housing. In some embodiments of the device, the cannula is slidably retractable relative to the housing. In some embodiments the device further comprises a locking guard member in communication with the one or more deployment members and configured to inhibit axial retraction of the cannula. In some embodiments of the device the locking guard member is removable from the housing to allow the one or more deployment members to engage the deployment shaft and to retract the cannula into the housing, wherein the one or more fluid channels remains stationary within the retracting cannula and acts to push the donor corneal tissue out of the cannula. In some embodiments of the device, the one or more deployment members comprises one or more deployment wheels.

In some embodiments of the device, the one or more fluid channels is configured to receive fluid and direct the fluid to the cannula to provide irrigation to the donor corneal tissue and the implantation site, and in some embodiments the one or more fluid channels is also configured to flowably expel the donor corneal tissue when the one or more deployment members is operated to cause the deployment shaft to retract the cannula and to deliver the donor corneal tissue to an implantation site from the flexible support retracted into the cannula.

Some embodiments of the device further comprise a fluid pressure source configured to releasably engage the delivery device and help deliver the corneal donor disc into a small incision scleral access site. In some embodiments the fluid pressure source comprises a syringe, hanging fluid bag or infusion pump.

In some embodiments of the device, the cannula is sized to enter an incision less than about 4 mm in length. In some embodiments at least a portion of the cannula is visually transmissive.

In some embodiments of the device, the removable reservoir comprises a reservoir base coupled to the distal end of the deployment shaft, a reservoir body removably coupled to the reservoir base, and a reservoir cap removably coupled to the reservoir body. In some embodiments, the reservoir base is removably coupled to the distal end of the deployment shaft. In some embodiments of the device, the fluid in the reservoir comprises a biocompatible fluid.

Another aspect of the disclosure is directed to a donor corneal tissue storage and delivery device kit, comprising a sterile package and a donor corneal tissue storage and delivery device in the sterile package. In some embodiments, the device comprises a housing having a proximal and distal end, a cannula, a fluid channel connector, at least one fluid channel, a flexible support, a retractor shaft, one or more loading members, a removable reservoir, a deployment shaft, and one or more deployment members.

In some embodiments, the cannula, having a proximal end and a distal end, is disposed at a distal end of the housing. In some embodiments the fluid channel connector is disposed at a proximal end of the housing. In some embodiments, the at least one fluid channel comprises a proximal end and a distal end, and in some embodiments, the proximal end of the at least one fluid channel is coupled to the fluid channel connector and the distal end is disposed proximate to within the proximal end of the cannula. In some embodiments, the flexible support is configured to receive donor corneal tissue and retract into the cannula. In some embodiments, the retractor shaft is coupled to the flexible support, and in some embodiments, the one or more loading members are held by the housing, coupled to the retractor shaft and operable to retract both the retractor shaft and coupled flexible support. In some embodiments, the flexible support and donor corneal tissue disposed on the flexible support are retracted into the cannula. In some embodiments the flexible support and donor corneal tissue adopt a rolled shape when retracted into the cannula.

In some embodiments the removable reservoir is in fluid communication with the fluid channel and configured to enclose the flexible support and cannula and to receive a volume of fluid for hydrating the donor corneal tissue received by the flexible support while the flexible support is retracted into the cannula. In some embodiments the deployment shaft is coupled to the cannula and configured to retract into the distal end of the housing. In some embodiments the one or more deployment members is coupled to the deployment shaft and operable to cause the deployment shaft to retract the cannula and to deliver the donor corneal tissue to an implantation site from the flexible support retracted into the cannula.

In some embodiments of the donor corneal tissue storage and delivery device the cannula tapers toward the distal end of the housing. In some embodiments of the device, the one or more fluid channels is configured to receive fluid and direct the fluid to the cannula to provide irrigation to the donor corneal tissue and the implantation site, and in some embodiments the one or more fluid channels is also configured to flowably expel the donor corneal tissue when the one or more deployment members is operated to cause the deployment shaft to retract the cannula and to deliver the donor corneal tissue to an implantation site from the flexible support retracted into the cannula.

Some embodiments of the device further comprise a fluid pressure source configured to releasably engage the delivery device and help a clinician to expel the corneal donor disc into a small incision scleral access site. In some embodiments the fluid pressure source comprises a syringe, hanging fluid bag or infusion pump.

In some embodiments of the device, the cannula is sized to enter an incision less than about 4 mm in length. In some embodiments at least a portion of the cannula is visually transmissive. And in some embodiments of the device, the cannula is slidably retractable relative to the housing.

In some embodiments the device further comprises a locking guard member in communication with the one or more deployment members and configured to inhibit axial retraction of the cannula. In some embodiments of the device the locking guard member is removable from the housing to allow the one or more deployment members to engage the deployment shaft and to retract the cannula into the housing, wherein the one or more fluid channels remains stationary within the retracting cannula and acts to push the donor corneal tissue out of the cannula. In some embodiments of the device, the one or more deployment members comprises one or more deployment wheels.

In some embodiments of the device, the removable reservoir comprises a reservoir base coupled to the distal end of the deployment shaft, a reservoir body removably coupled to the reservoir base, and a reservoir cap removably coupled to the reservoir body. In some embodiments, the reservoir base is removably coupled to the distal end of the deployment shaft. In some embodiments of the device, the fluid in the reservoir comprises a biocompatible fluid.

It is noted that any of the features claimed with respect to one type of claim, such as a system, apparatus, may be claimed or carried out as any of the other types of claimed operations or features.

Further features, advantages and details of the present disclosure will be appreciated by those of ordinary skill in the art from a reading of the figures and the detailed description of the embodiments that follow, such description being merely illustrative of the present disclosure.

BRIEF DESCRIPTION OF THE DRAWINGS

FIGS. 15A and 15B are partial top views of exemplary flexible support configurations with releasable and integral arms, respectively, according to embodiments of the present disclosure.

FIGS. 16A-16C are top schematic views of exemplary flexible tissue support configurations according to embodiments of the disclosure.

FIGS. 17A-7C are side views of flexible substrates for receiving donor tissue during a harvesting procedure according to some embodiments of the present disclosure.

DETAILED DESCRIPTION

Figure 1:
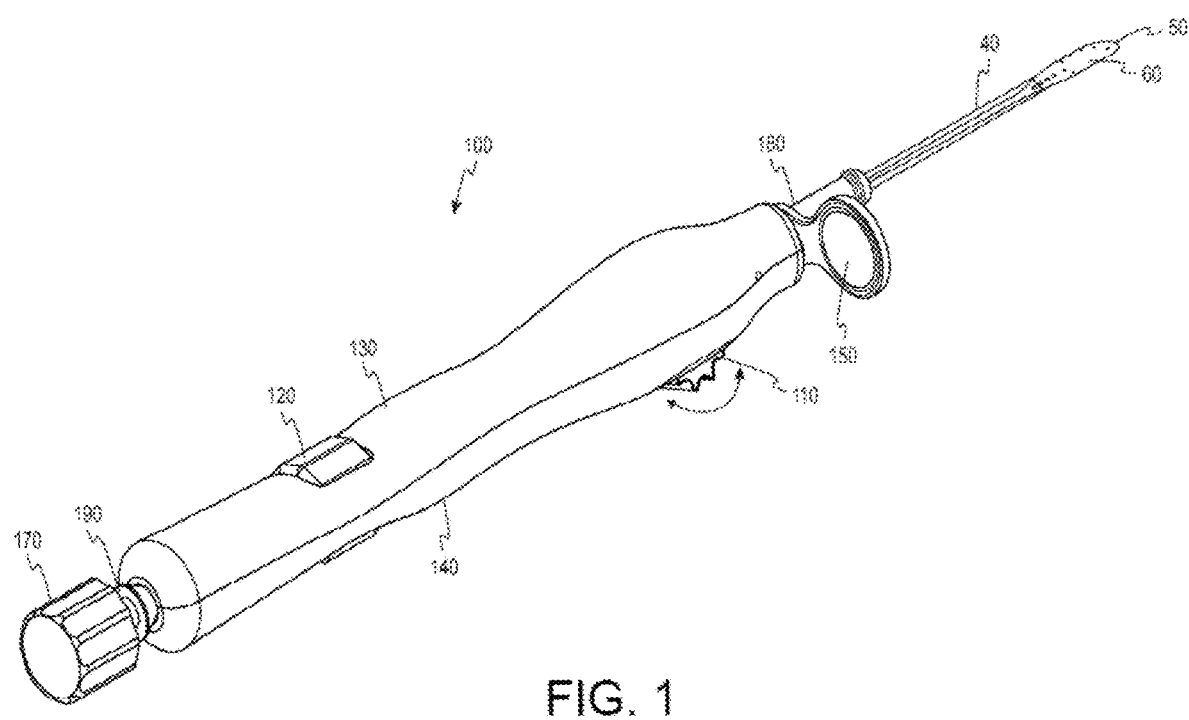
FIG. 1 is a schematic bottom perspective view of a device according to some embodiments of the present disclosure with a flexible support in an extended position.

Embodiments are described more fully with reference to the accompanying drawings. Aspects of the present disclosure may, however, be embodied in many different forms and should not be construed as limited to the embodiments set forth herein. Rather, these embodiments are provided so that the present disclosure will be thorough and complete, and will fully convey the scope of the present disclosure to those skilled in the art.

FIGS. 1-10 illustrate an exemplary embodiment of a device 100 that can be a multi-purpose, bidirectional tool that receives donor tissue, holds the donor tissue, then is used to surgically deliver the donor tissue implant 60. As shown in FIGS. 1-2 and FIGS. 9-10, the device 100 includes a flexible support 50 that is configured to hold the donor tissue graft 60. The support 50 may be a biocompatible, pre-shaped carrier. The device 100 may include a retractor wheel 120 coupled to the support 50.

Figure 2:
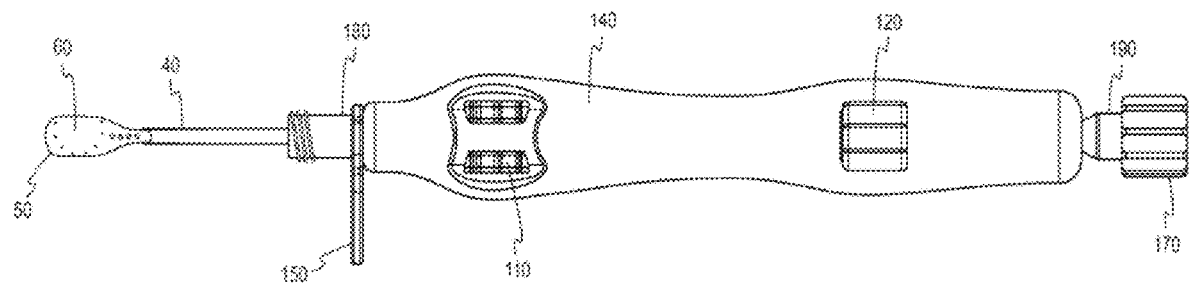
FIG. 2 is a schematic top view of a device according to some embodiments of the present disclosure with a flexible support in an extended position.
Figure 3:
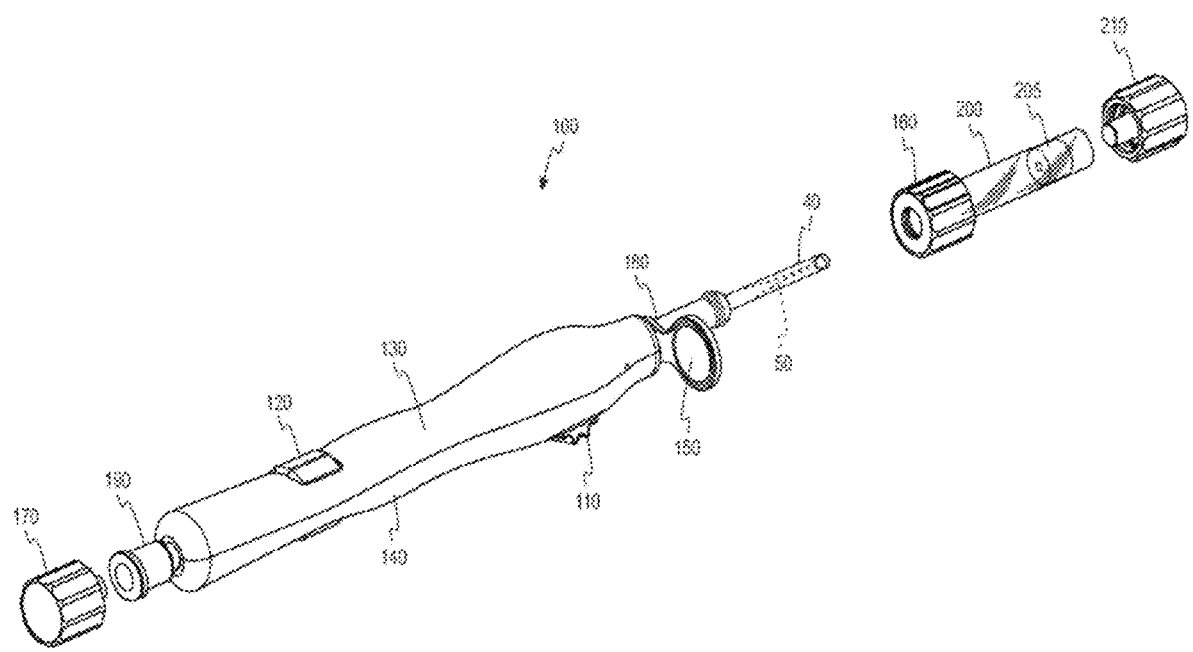
FIG. 3 is a schematic of a partially exploded bottom perspective view of a device according to some embodiments of the present disclosure with a flexible substrate loaded with donor tissue and retracted into a cannula.
Figure 4:
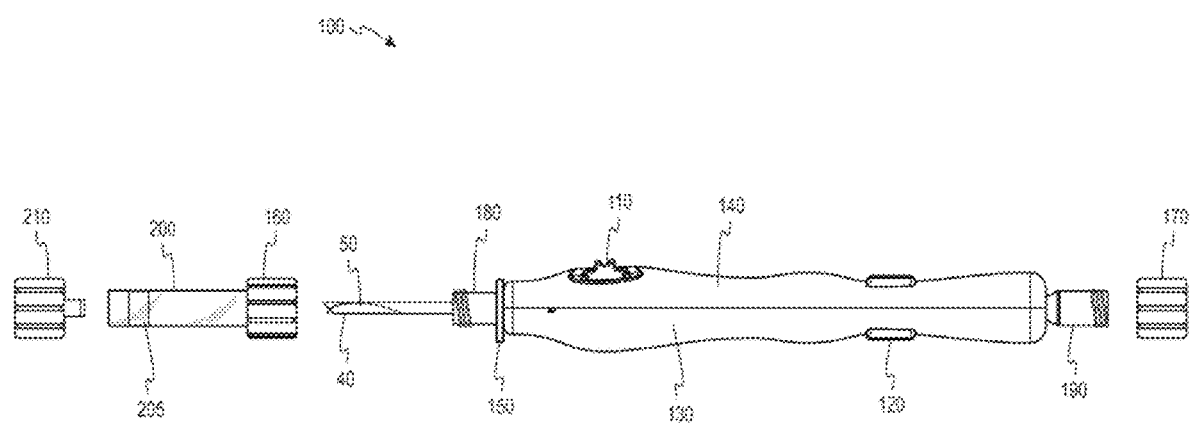
FIG. 4 is a schematic of a partially exploded side view of a device according to some embodiments of the present disclosure with a flexible substrate loaded with donor tissue and retracted into a cannula.
Figure 5:
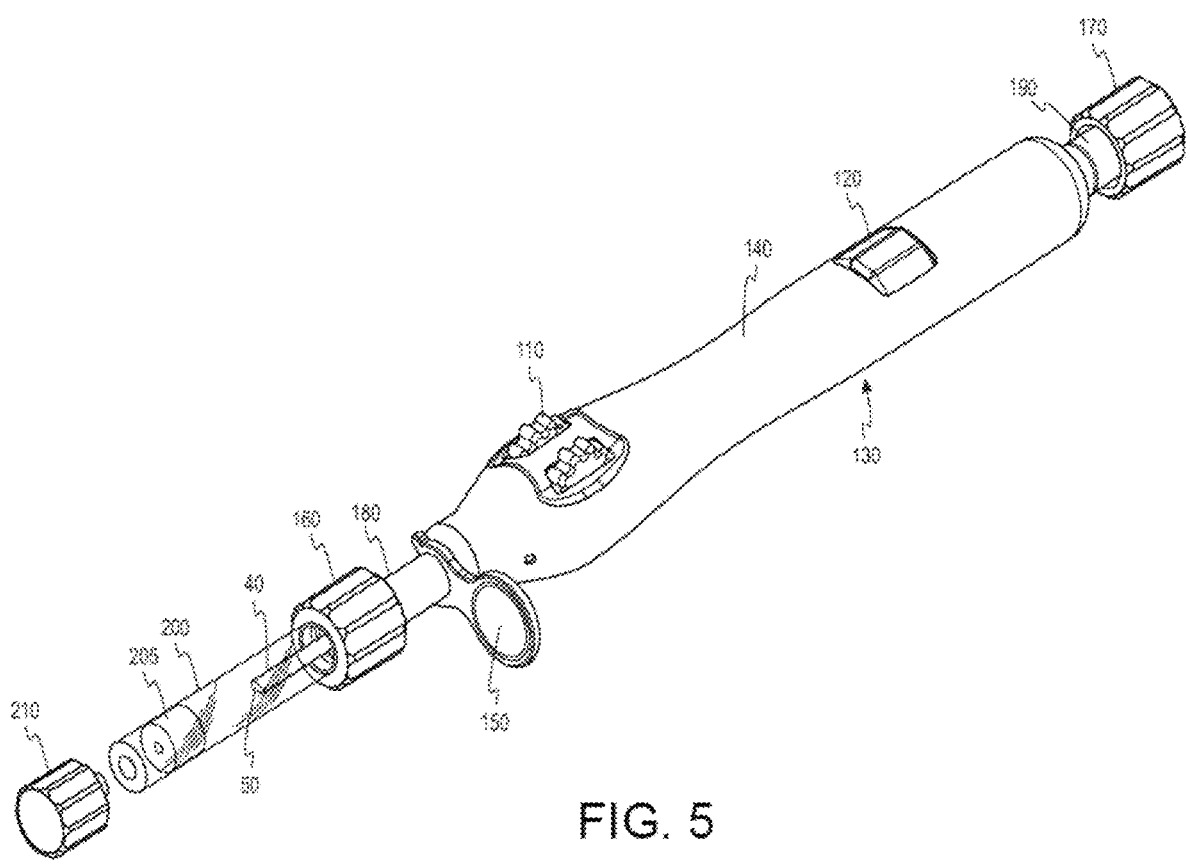
FIG. 5 is a schematic top perspective view of a device according to some embodiments of the present disclosure with a flexible substrate loaded with donor tissue and retracted into a cannula and a reservoir body attached to the device.
Figure 6:
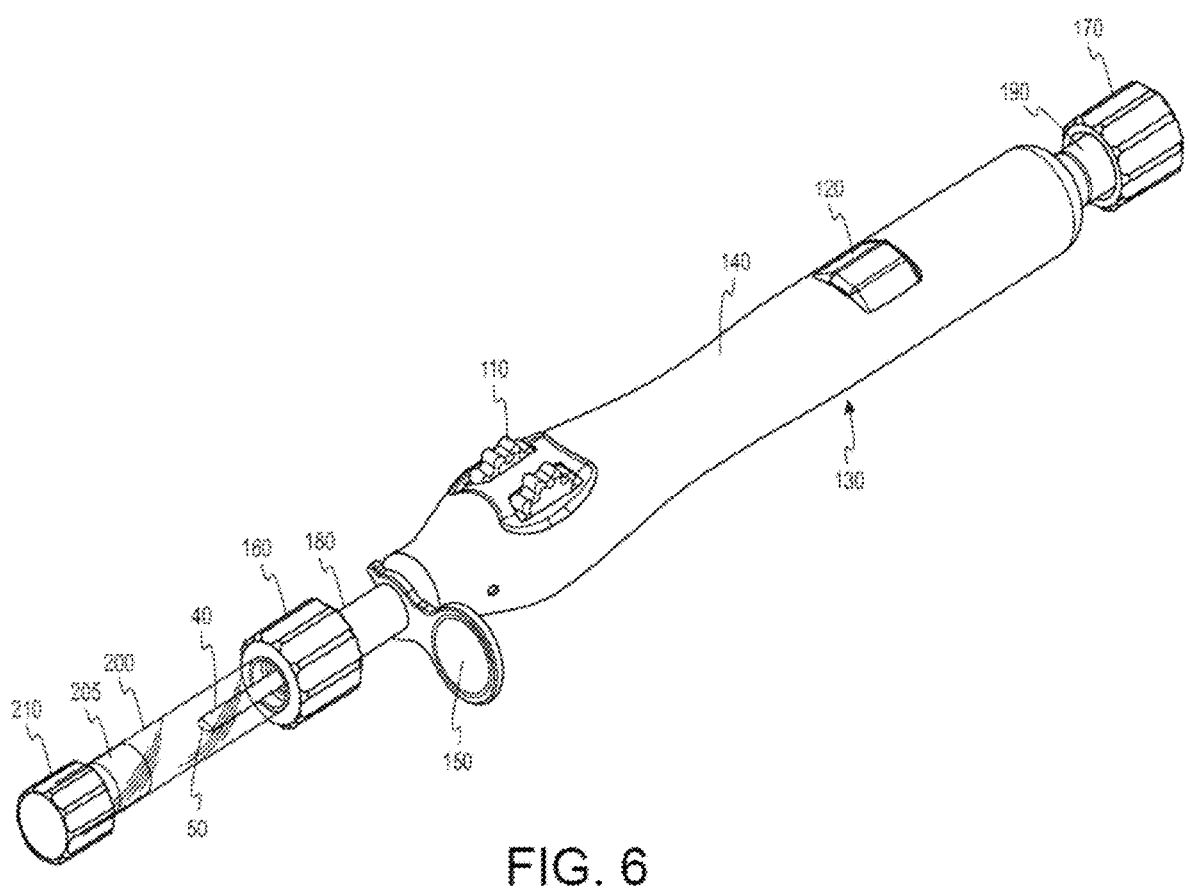
FIG. 6 is a schematic top perspective view of a device according to some embodiments of the present disclosure with a flexible substrate loaded with donor tissue and retracted into a cannula and a reservoir body and reservoir cap attached to the device.
Figure 7:
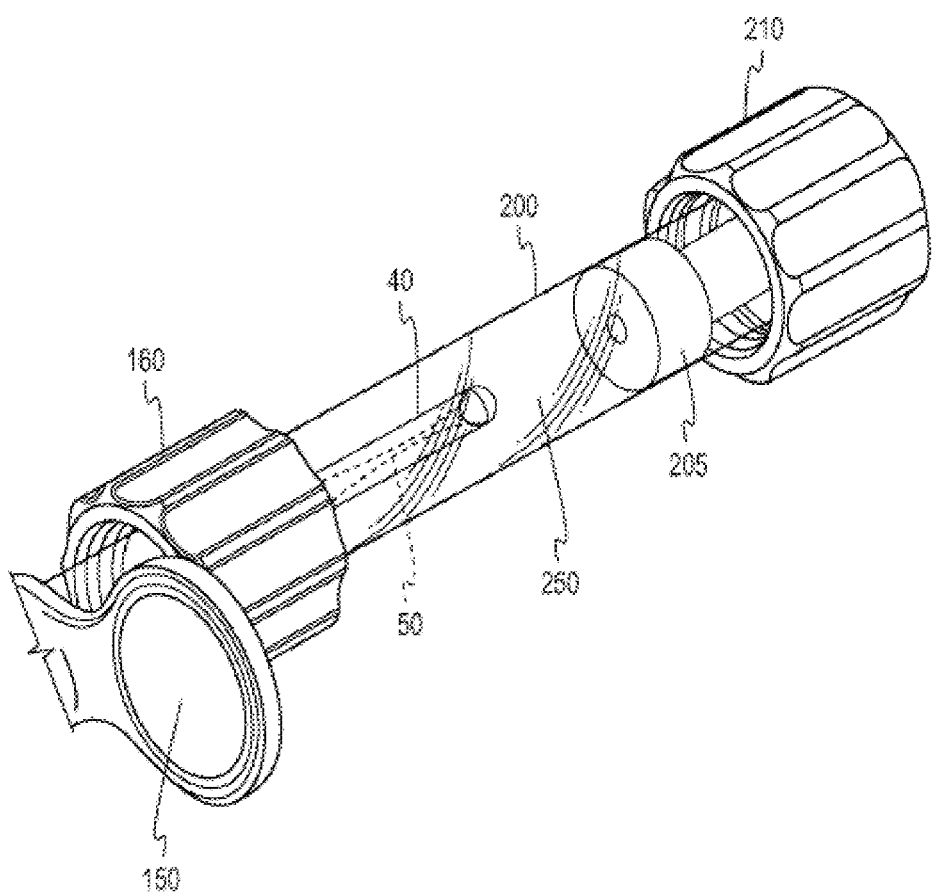
FIG. 7 is an enlarged schematic partial perspective view of the reservoir end of the device shown in FIG. 6 with reservoir cap in place and filled with biocompatible fluid.

The device 100 also includes a holding chamber defined in part by a cannula 40. By rotating the retractor wheel 120 in the direction of a printed arrow on the device body as shown in FIG. 2, the support 50 translates from an empty (ready to load) configuration for receiving the donor tissue graft 60 as shown in FIGS. 1-2, to a retracted hold configuration within the cannula 40 after receiving the donor tissue graft 60 as shown in FIGS. 3-4. As such, the donor tissue graft 60 is drawn into the cannula 40 for subsequent implantation. As described below, deployment wheels 110 may be used to retract the cannula 40 into the device body 100 and deploy the donor tissue graft 60 during an implant procedure.

Figure 8:
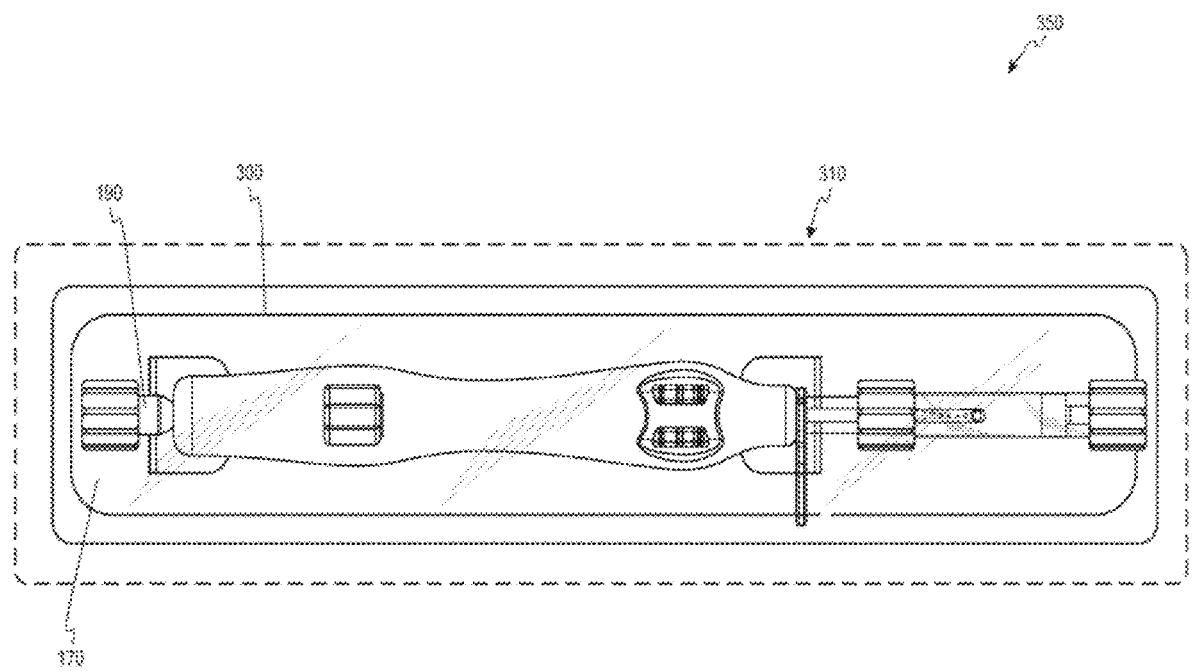
FIG. 8 is a schematic illustration of a donor corneal implant tissue storage and delivery device kit according to embodiments of the present disclosure.

As illustrated in FIGS. 3-8, a reservoir body 200 and reservoir cap 210 may be used to enclose the donor tissue 60 loaded with the support 50 into the cannula 40. The reservoir can be filled with a preferably sterile biocompatible fluid 250, such as cornea storage solution, Optisol, Optisol GS, Dexsol, McCarey-Kaufman Media, Life 4° C. solution, sterile water, saline, viscoelastic material and the like. Additionally, a sterile package 310 as shown in FIG. 8 may be used to encase the loaded device 100. The sterile package 310, for instance, may be a biocompatible, sterile pouch, container or bag. The support 50 can be kept in the hold configuration while the device 100 is packaged in the sterile package 310 for longer term storage and shipment. Alternatively, the device 100 can be loaded at the clinical site at the time of implant procedure.

Figure 9:
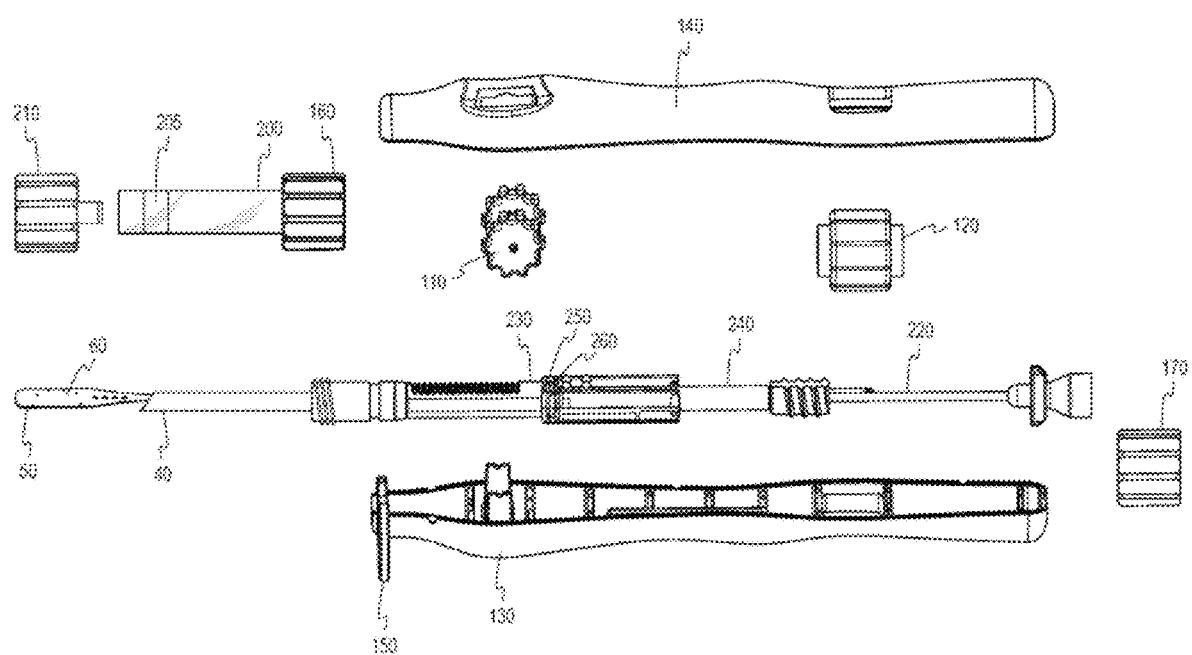
FIG. 9 is an exploded side view schematic of a device according to some embodiments of the present disclosure with a flexible tissue support in an extended position, not loaded with donor tissue.

The forward end portion of the cannula 40 can include a tapered end as visible in FIG. 9 and can have a size (cross-sectional area and/or diameter) that allows the cannula 40 to be inserted at least partially through an incision in the cornea to implant the donor tissue graft 60. During the implant procedure, deployment wheels 110 can be rotated to retract the cannula 40 and the support 50 and to position the donor tissue graft 60 at the implantation site as described further below. To inhibit inadvertent and/or premature release and/or exposure of the implant tissue 60 from the device 100, the deployment wheels 110 can cooperate with a locking guard 150. The locking guard 150 can be configured to inhibit extension of the cannula 40 and support 50 until actual delivery of the donor tissue graft 60 is desired.

In some embodiments, at least the forward portion of the cannula 40 can be visually transmissive to allow a user to confirm the position of the donor tissue graft 60 and/or support 50.

Figure 10:
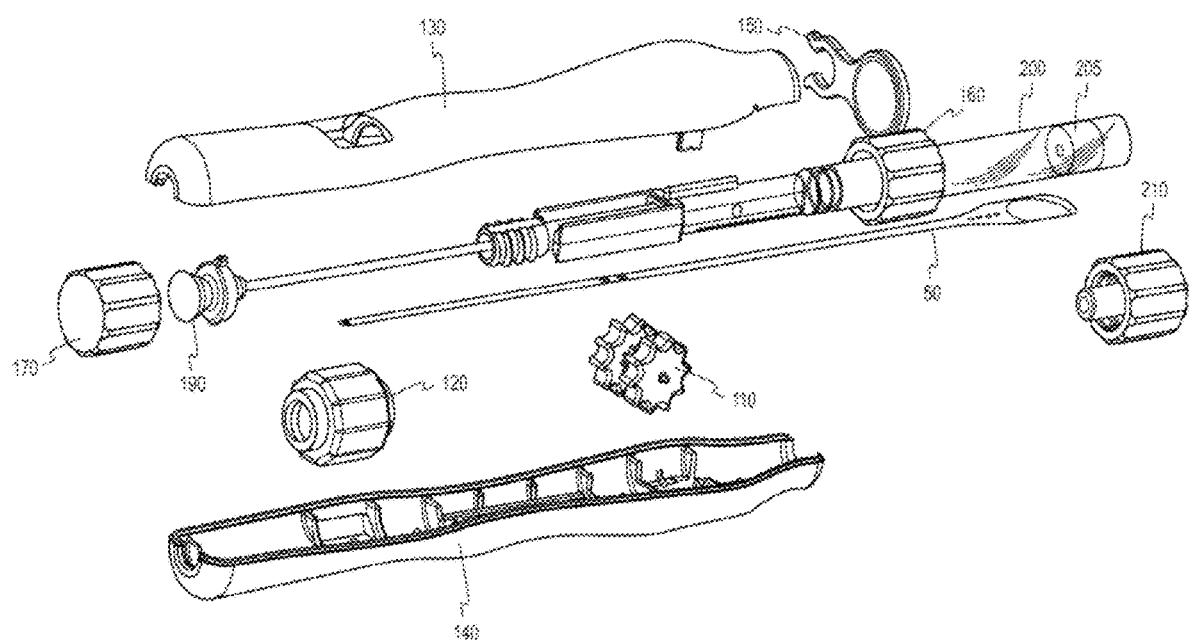
FIG. 10 is an inverted exploded side view schematic of a device according to some embodiments of the present disclosure.

As shown in FIGS. 9-10, the device 100 can also include a fluid channel 220 held with an end portion residing inside the cannula 40 in communication (upstream but proximate to) with the donor tissue graft 60. The device 100 can be configured to provide flow-through irrigation via the fluid channel 220 for deploying the donor tissue graft 60 and/or maintain recipient eye chamber depth. In operation, the fluid channel 220 can be configured to remain substantially stationary both during initial loading of this support 50 with the donor tissue graft 60 into the cannula 40, and while the cannula 40 are axially retracted. The fluid channel 220 may be configured to facilitate the ejection of the donor tissue 60 from the device 100. The fluid channel 220 may be configured to deliver pressurized fluid from a pressurized fluid flow source (such as a syringe, a cylinder, hanging fluid bag, infusion pump, or other flow source) reversibly coupled to the fluid channel connector 190. The fluid channel 220 can contact the donor tissue graft 60 directly and/or flowably direct fluid to contact the donor tissue graft 60. The fluid channel 220 can also deliver or push an intermediate fluid such as a gel (comprising, for example, a viscoelastic material) against a trailing edge of the donor tissue graft 60 to eject the tissue from the cannula 40 into a patient.

In some embodiments, the device 100 can provide a practitioner with substantially atraumatic donor corneal tissue handling and can promote precision placement of donor tissue graft 60 in a recipient's anterior chamber. The donor tissue graft 60 can also be substantially atraumatically unsheathed in the recipient eye.

FIG. 8 illustrates a donor corneal implant tissue storage and delivery device kit 350. The support 50 of the sterile device 100 can be loaded with the donor tissue graft 60 under aseptic conditions and thus converted to the donor corneal implant tissue storage and delivery device kit 350. When assembling the kit 350, the fluid channel 220, cannula 40, and the reservoir body 200 are all preferably filled with biocompatible storage fluid 250 before optionally mounting the device 100 on a tray 300 and sealing the device 100 and the tray 300 (if present) in a sterile package 310. The sterile package 310 may be configured to releasably hold the sterile device 100 in the absence of a tray 300, e.g., by shaping or otherwise molding the interior of the sterile package 310 to do so. The sterile package 310 may also be a substantially cylindrical in shape comprising a body and with a cap, which body may include any coupling mechanism, e.g., threads, friction fit, and the like, to reversibly engage the body. Accordingly, the kit 350 includes the device 100 where the support 50 is loaded with the donor tissue graft 60, which is bathed in biocompatible storage fluid 250 within a reservoir body 200 closed with a removable cap 210.

Together, the package 310 and, optionally, the tray 300 can provide a flexible package, such as an elastomeric- or foil-backed elastomeric package, or a rigid substrate package. In general, various combinations of flexible and/or rigid packaging materials can also be used. The kit 350 and/or device 100 can be labeled as single-use disposable.

The device 100 (at least the device body or housing thereof, bottom cover 130 and top cover 140) may comprise a sufficiently strong and relatively rigid elastomer, composite, polymer, plastic or ceramic or may comprise a metal, such as stainless steel.

In some embodiments, the device 100 in the kit 350 may also be provided in the empty configuration, where the support 50 is not loaded with the donor tissue graft 60. With an unloaded device, the fluid channel 220 may be devoid of the biocompatible fluid 250. The reservoir base 160, reservoir body 200 and the reservoir cap 210 may be attached to the device 100 or provided separately within the kit 350. A kit 350 with an unloaded device 100 can be delivered to a facility that processes the donor tissue graft 60 and where the device 100 can be loaded with the donor tissue graft 60. The kit 350 with the loaded device can then be further delivered to a practitioner for use in an implant procedure.

FIG. 9 illustrates an exploded side view schematic of a device according to some embodiments of the present disclosure. In some embodiments, the device 100 comprises a bottom cover 130 that, in cooperation with a top cover 140, securely holds operative elements of the device 100 and can be referred to as the device body or housing. The reservoir base 160, reservoir body 200 and the reservoir cap 210 are disposed at a distal end of the device 100. The assembled body 100 holds a fluid flow connector 190 at a proximal end of the device 100. The fluid flow connector 190 is leaklessly attached to the fluid channel 220, which extends through a retractor shaft 240 and a deployment shaft 230 to the cannula 40. When the support 50 loaded with the donor tissue graft 60 is retracted into the cannula 40 by operation of the retractor wheel 120, the fluid channel 220 is proximally disposed relative to the retracted carrier support 50.

The fluid channel 220 can be configured to engage a pressurized fluid flow source (such as a syringe, a cylinder, hanging fluid bag, infusion pump, or other flow source). A fluid channel cap 170 covers the fluid flow connector 190 at the distal end of the device 100. After removing the fluid channel cap 170, the pressurized fluid flow source can be coupled to the fluid flow connector 190. The fluid flow connector 190 may employ any coupling mechanism, e.g., Luer-Lok, friction fit and the like. The fluid channel 220 is fluidly coupled to the cannula 40 and the reservoir (base 160, body 200 and cap 210). A distal end of the fluid channel 220 may be disposed inside the cavity of the cannula 40 (i.e., disposed within the proximal end of the cannula). When the support 50 is retracted into the cannula 40, the cannula 40 defines an outermost concentric layer, support 50 defines an intermediate concentric layer, and the distal end of the fluid channel 220 defines an innermost concentric layer. The fluid channel 220 remains fixed relative to the device body 100 band does not move during operation of the retractor wheel 120 or the deployment wheels 110. When the deployment wheels 110 are rotated to retract the cannula 40 and the support 50 retract into the body of the device 100b, the distal end of the fluid channel 220 blocks retraction of the donor tissue 60 and acts as a tissue delivery member by pushing the donor tissue graft 60 off the support 50 and out of the cannula 40. The donor tissue graft 60 is delivered from the device 100 to the implantation site. Thus, with the donor tissue graft 60 positioned on the support 50 in the cannula 40, the practitioner can insert the cannula 40 into the cornea and manipulate the device 100 to orient the donor tissue graft 60, and then retract the cannula 40 to push the donor tissue graft 60 into position at the implantation site.

The retractor shaft 240 securely attaches to a shaft portion 50r of the support 50, enabling them to move in unison. The retractor shaft 240 slidably engages the deployment shaft 230. A proximal portion of the retractor shaft 240 is treaded to threadably engage the retractor wheel 120 such that when the retractor wheel 120 is rotated in the direction of the arrow shown in FIG. 2, the retractor shaft 240 and support 50 are retracted, proximally, in unison, with the support 50 visibly retracting into the cannula 40. In certain embodiments, the threaded portion of the retractor shaft 240 and the retractor wheel 120 are configured to allow a desired amount of travel before the threaded portion of the retractor shaft 240 exceeds the thread travel of the retractor wheel 120 and they disengage.

The deployment shaft 230 is located in the distal end of the device body 100b. The proximal end of the deployment shaft 230 is slidably engaged with the retractor shaft 240. In certain embodiments, the junction between the deployment shaft 230 and the retractor shaft 240 is made leak proof or leak resistant by a 1-way valve or gasket 250 and a gasket cover 260. The 1-way valve or gasket 250 is preferably located distally relative to the gasket cover 260 to ensure fluid contained in the fluid channel 220, the cannula 40, and the reservoir 200 do not leak into the device body 110b and to prevent the donor tissue graft 60 loaded in the device 100 to dry out or otherwise become compromised. The gasket cover 260 can provide structural support and rigidity to the 1-way valve or gasket 250.

A medial portion of the deployment shaft 230 includes teeth extending radially from the longitudinal axis of the deployment shaft 230. In the embodiment illustrated in FIG. 9, deployment wheels 110 are arranged about opposite ends of an axel, which has teeth that engage the teeth on the deployment shaft 230. The deployment wheels 110 and the deployment shaft 230 are matably engaged so that rotating the deployment wheels causes the shaft 230 to move fore or aft, depending on direction of rotation of the deployment wheels 110. When the deployment shaft 230 is in an extended position (as shown in FIG. 9),the locking guard 150 can removably engage the shaft 230 to prevent retraction into the device body 100b. In some embodiments, the locking guard 150 engages a circumferential groove in the shaft 230.

A deployment shaft distal end 180 (located in the distal portion of the deployment shaft 230) is coupled to the cannula 40. In certain embodiments, the cannula 40 is substantially transmissive to light so that the practitioner can see into the cannula 40. A reservoir base 160 may include any coupling mechanism, e.g., Luer-Lok, friction fit, threads and the like, to reversibly and leaklessly engage the deployment shaft distal end 180, which, in such embodiments, itself includes any coupling mechanism complementary to the reservoir base 160. In certain embodiments, the reservoir base 160 can freely rotate on the deployment shaft 230 while being retained thereon, while in other embodiments, the reservoir base 160 is fixed to the deployment shaft 230 and in preferred embodiments, the reservoir base 160 is removable from the deployment shaft 230.

The interior surface of the reservoir base 160 may also include any coupling mechanism, e.g., Luer-Lok, friction fit, threads and the like, to reversibly and leaklessly engage a proximal portion of the reservoir 200. In some embodiments, the reservoir base 160 and the reservoir 200 are permanently or otherwise irreversibly engaged or molded or otherwise constructed as/in one piece. The distal end of the reservoir 200 can reversibly and leaklessly engage the reservoir cap 210. The combination of the reservoir base 160, the reservoir 200, and reservoir cap 210 form a leakless chamber capable of holding one or more fluids. In certain embodiments, the one or more fluids may include a sterile biocompatible fluid 250 (e.g., cornea storage solution, Optisol, Optisol GS, Dexsol, McCarey-Kaufman Media, Life 4° C. solution, sterile water, saline, viscoelastic material, and the like, and combinations thereof). In certain embodiments, the reservoir 200 is of sufficient length and diameter to enclose the cannula 40 and the support 50 while the support 50 is in extended from the cannula 40. In other embodiments, the reservoir 200 is of sufficient length and diameter to cover the cannula 40 and support 50 while the support 50 is retracted into the cannula 40. The reservoir 200 may include a fluid flow restrictor 205. The fluid flow restrictor 205 can be molded with the reservoir 200, press fit, or otherwise irreversibly engaged in or with the interior of the reservoir 200. The fluid flow restrictor 205 comprises one or more apertures or holes fluidly connecting the proximal and distal ends of the reservoir 200. The one or more apertures or holes may be arranged along the long axis of the reservoir through the fluid flow restrictor 205. The fluid flow restrictor 205 may reduce the flow rate through fluid channel 210 by at least about 1%, or about 5%, or about 10%, or about 15%, or about 20%, or about 25%, or about 30%, or about 35%, or about 40%, or about 45%, or about 50%, or about 55%, or about 60%, or about 65%, or about 70%, or about 75%, or about 80%, or about 85%, or about 90%, or about 95%, or about 99%. The fluid flow restrictor 205 may also allow an adjustable fluid flow restriction.

FIG. 10 illustrates and inverted exploded side view schematic of a device according to some embodiments of the present disclosure.

Figure 11:
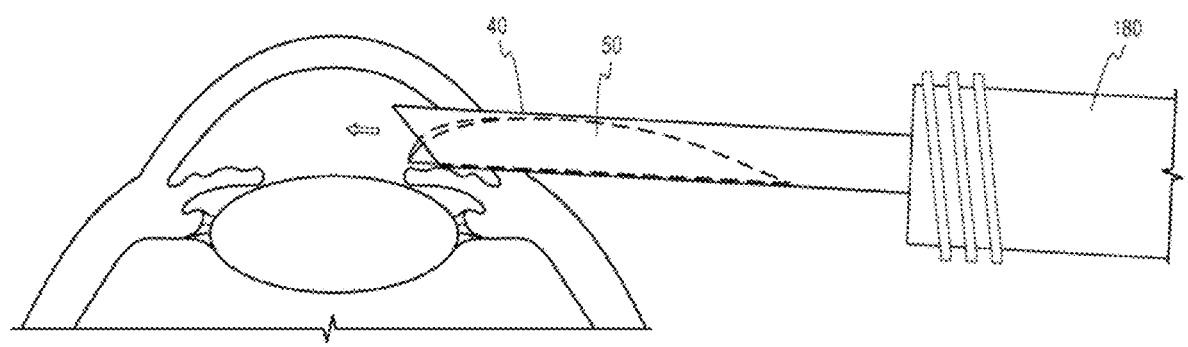
FIG. 11 is a schematic illustration of the device and rolled donor disc being delivered to a recipient stromal bed to carry out small incision procedures (e.g., DLEK, DSEK or DSAEK) according to embodiments of the present disclosure.

FIG. 11 illustrates an exemplary surgical introduction of the device 100 to insert a rolled donor tissue graft 60 into position at an implantation site. As shown, fluid can be introduced into the cannula 40 from the fluid channel 220 and directed provide irrigation to the surgical site and to the donor tissue. The cannula 40 can be retracted to help expel the donor tissue 60. As described above, in certain embodiments the fluid channel 220 is arranged concentrically within the cavity of the cannula such that when the support 50 is retracted in a "loaded" configuration, the cannula 40 comprises the outermost concentric layer, followed by the support 50, then the proximal end of the fluid channel 220. In certain embodiments, the fluid channel is fixed place and does not move upon engagement of the retractor wheel 120 or the deployment wheels 110. In these embodiments, when the deployment wheels 110 are rotated such that the cannula 40 and the support 50 retract toward or into the body of the device 100b, the proximal end of the fluid channel 220 blocks retraction of the donor tissue 60 thereby acting as a tissue delivery member, "pushing" the donor tissue out of the retracting cannula 40 and into the delivery site of a patient's eye. Fluid from the fluid channel can also help flowably expel the rolled disc into position.

Figure 12A:
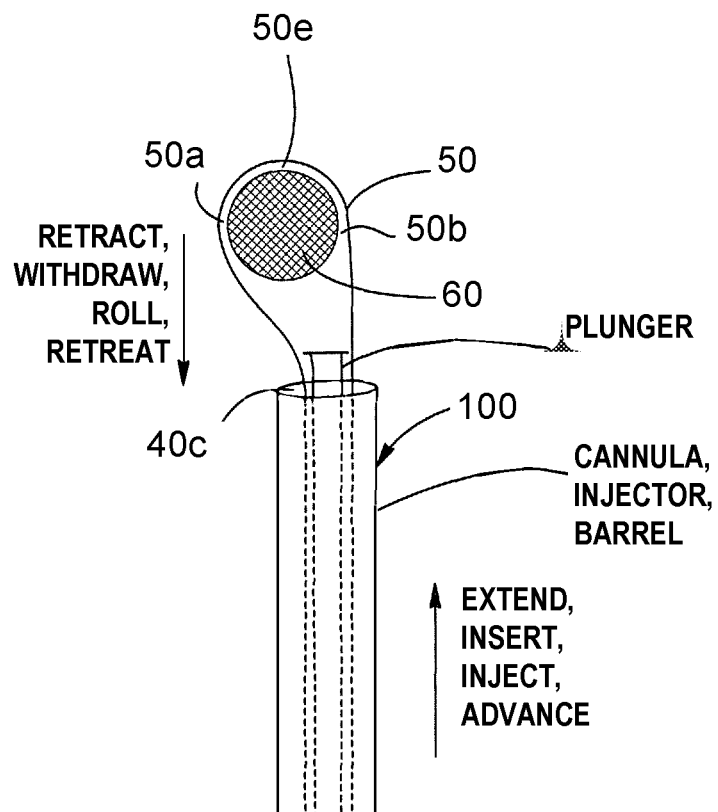
FIG. 12A is a schematic illustration of the anterior end of a device according to embodiments of the present disclosure.

FIG. 12A illustrates a donor implant tissue storage and delivery device 100 and a donor tissue graft 60. The donor implant tissue is typically a thin donor graft of posterior corneal stroma, Descemet's membrane, and endothelium, although other tissue grafts, particularly fragile tissue grafts, may be suitable for forming and/or delivery using devices/methods described herein. As described above, the device 100 includes the support 50 that holds the donor implant tissue 60. The holding portion 50e of the support 50 can be configured to have a substantially planar shape outside the device 100.

Figure 12B:
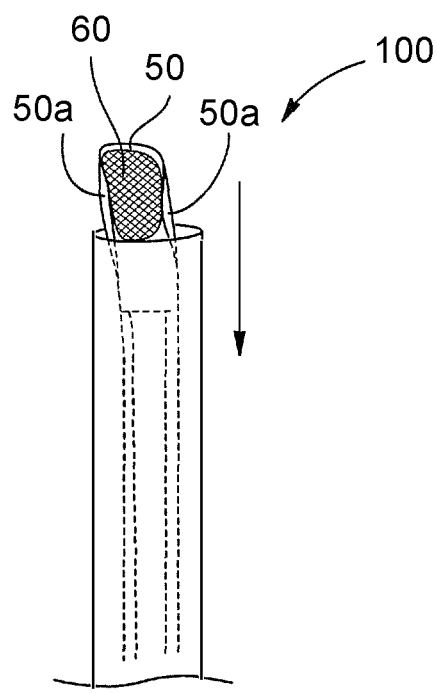
FIG. 12B is a schematic illustration of the device shown in FIG. 12A showing the flexible substrate and donor tissue graft being retracted into a cannula/holding chamber according to embodiments of the present disclosure.
Figure 13A:
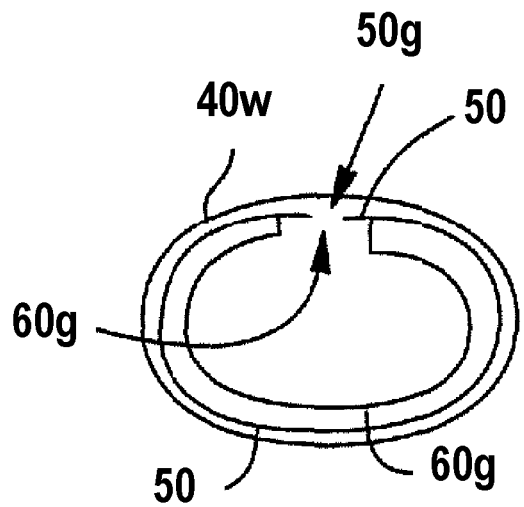
FIGS. 13A-13C are exemplary cross-sectional views across the canula bisecting the flexible tissue support and donor tissue.
Figures 13B, 13C:
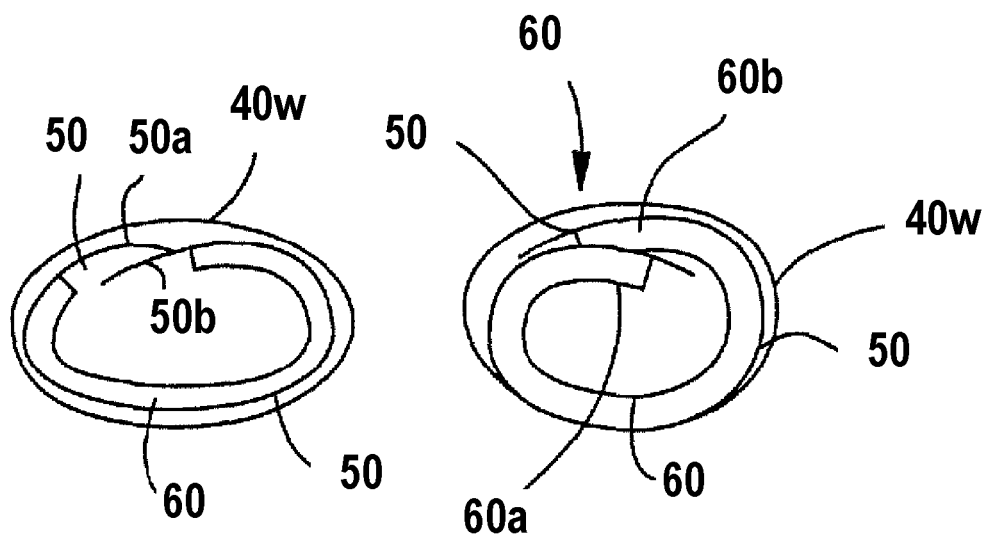
Figure 14:
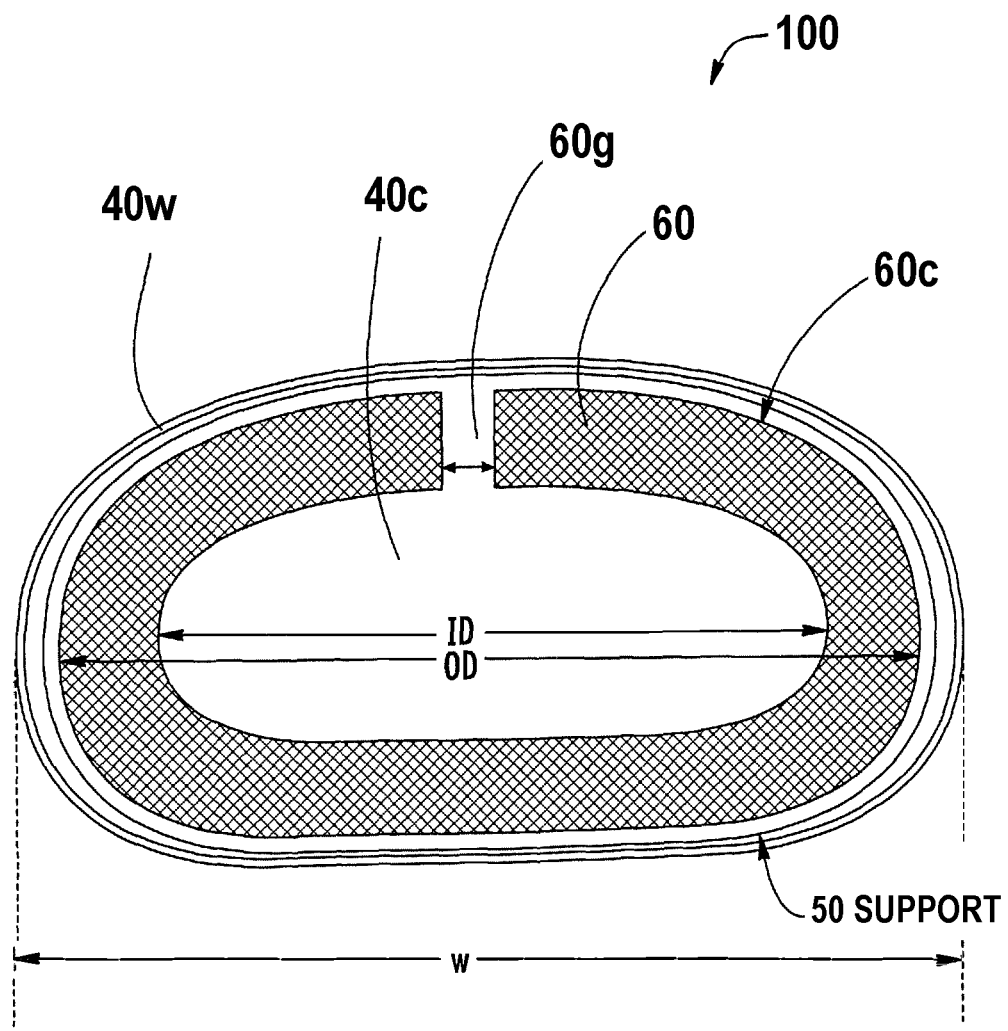
FIG. 14 is a greatly enlarged cross-sectional view of the device shown in FIGS. 12A and 12B with a fully retracted flexible substrate with tissue graft according to some embodiments of the present disclosure.

As shown in FIGS. 12A and 14, the cannula 40 includes a cannula cavity 40c that is configured to slidably receive the support 50 which holds the donor tissue graft 60. As shown in FIG. 12B, as the support 50 is retracted into the cannula cavity 40c, the outer edges 50a, 50b of the support 50 are pushed inwardly together to roll the support 50, thereby rolling the donor tissue graft 60 into a smaller, compact shape. The support 50 is sufficiently flexible so as to substantially conform to the shape of the cannula cavity wall 40w as shown in FIGS. 13A-C. In general, the donor tissue graft 60 takes on the shape of the support 50.

When the support 50 and the donor tissue graft 60 are retracted into the cannula 40, the support 50 and the donor tissue graft 60 can assume a rolled shape as shown in FIG. 13A, where there are respective gaps gaps 60g, 50g between the opposing edges, i.e., the opposing edges do not contact each other. Alternatively, the edges 50a, 50b of the support 50 may contact and even overlap as shown in FIG. 13B. Optionally, as shown in FIG. 13C, the donor tissue disc 60 may be shaped so that one edge 60a rolls under the opposing edge 60b. It is noted that the cross-sectional shape of the cannula cavity 40c is shown in FIGS. 14 and 13A-13C as being substantially oval or circular; however, the present disclosure is not limited thereto. Other geometric shapes may also be employed, such as, for example, pentagonal, hexagonal, square, rectangle, triangular, and the like.

As shown in FIG. 14, the carrier support 50 can be pushed, folded, wrapped or bent, and is typically formed to have a curvilinear cross-sectional shape 50c with the two opposing edge portions spaced apart to define the gap 50g. However, the support 50 as well as donor tissue graft 60 can assume other shapes. The donor tissue graft 60 can assume a rolled shape without sharp fold creases, corners or edges. As shown, the curvilinear shape 50c can be substantially oval with rounded lateral edges. The cannula cavity 40c can have a width W that is between about 3-6 mm, typically between about 3.5 mm to about 4 mm. The outside diameter (OD) of the donor implant tissue graft in the shaped configuration 50c can be between about 2.5 mm to about 3 mm, typically about 2.87 mm for a 9 mm graft. The inside diameter (ID) of the shaped donor tissue disc 50c can be between about 0.1 mm to about 0.5 mm less than the OD, depending on thickness of the donor tissue graft 50. For the 2.87 mm OD and a tissue graft having a thickness of about 150 μm, the ID can be about 2.84 mm.

The support 50 can be formed from a unitary layer of biocompatible material or laminated layers of biocompatible materials. The support 50 can comprise any suitable biocompatible material, such as elastomer, polymer, and copolymer materials and/or derivatives thereof, mylar, foil and the like, and/or combinations thereof. Biocompatible non-stick and/or antifriction coatings may be used. The support 50 can include a first anti-friction coating on one primary surface and a different coating on the tissue-contacting surface. The support 50 can be a thin-film substrate.

As shown in FIG. 14, the carrier support 50 can be thinner than the donor tissue graft 60. In some embodiments, the support 50 is less than half the thickness of the donor tissue graft 60. In particular embodiments, the support 50 can be between about 1-200 μm thick, and more typically between about 10-100 μm thick.

FIG. 15A illustrates that the carrier support 50 can be attached to a shaft 51. The shaft 51 can be rigid or have greater rigidity with respect to the carrier support 50. The shaft 51 can be releasably or fixedly attached to the support 50. FIG. 15B illustrates that the carrier support 50 can include an integral, rearwardly extending shaft 50r that extends away from a holding portion 50e of the support 50. The shaft 50r may be attached to a stiffening member or may be laminated or otherwise structurally reinforced for increased rigidity. The shaft 51, 50r can engage the support 50 and be used to pull the substrate into the cannula cavity 40 of the device 100. The donor tissue graft 60 is placed on a first surface of the support 50 with the stroma side contacting the support 50. The support 50 is then retracted into the cannula cavity 40c. The device 100 is rotated to place the stroma side up, with the endothelium side facing down. The end of the device 100c can be inserted into the eye's anterior chamber and the donor tissue graft 60 ejected, expelled or otherwise released.

FIGS. 16A-16B illustrate exemplary paddle-like configurations for the distal portion 50e for holding the donor tissue graft 60. As shown in FIG. 16A, the distal portion 50e can have a rectangular body with a rounded corners. As shown in FIG. 16B, the distal portion 50e can be substantially circular. As shown in FIG. 16C, the support 50 can include visual alignment indicia 55 for facilitating proper placement during the harvesting procedure. In some embodiments, the support 50 can include a well or a depression formed in the support 50 or an aperture. The well can reduce surface tension to facilitate the ability of the support 50 to roll when retracted into the cannula 40.

In some embodiments, the device 100 can be configured to inhibit rotation of the support 50 inside the cannula cavity 40c to positively control and maintain the orientation of the support 50. In this arrangement, the stromal and endothelial sides are known and controlled, oriented to a user's control, and/or positioned so that the orientation for placement can be easily determined or known.

Figure 17A:
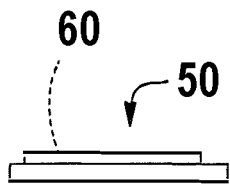
Figure 17B:
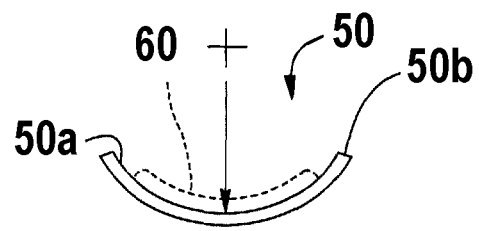
Figure 17C:
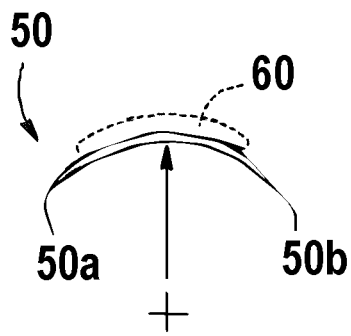

FIGS. 17A-17C illustrate exemplary configurations of the support 50 when receiving the donor tissue graft 60 from a harvesting procedure. The donor implant tissue 60 can be placed on the support 50 when the distal portion 50e is unrolled and substantially planar as shown in FIG. 17A. In other embodiments, the support 50 may be configured to have a concave or convex surface as shown in FIGS. 17B-C, respectively. The donor implant tissue 60 can be placed on an upper surface of the support 50, then rolled into a more compact shape. If the support 50 has a concave or convex curvature, the rolling may follow the direction of the curvature. For example, the outer edges 50a, 50b can be rolled upward for the configuration shown in FIG. 17B and the outer edges 50a, 50b can be rolled downward in the embodiment shown in FIG. 17C.

Figure 18:
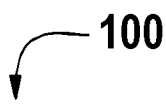
FIG. 18 is a schematic side view of the cannula with flexible tissue support fully retracted, loaded with donor implant tissue illustrating an implant orientation of the donor implant tissue in the device according to some embodiments of the disclosure.

FIG. 18 illustrates that the device 100 can have a harvest configuration and a delivery configuration for receiving and deploying, respectively, the donor tissue graft 60. As shown, it is desirable to have the endothelium side of the tissue facing upward and the stromal side oriented (facing) down during harvest or preparation, and to reverse the orientation for ease of placement upon release of the implant from the cannula cavity 40c. As the implant leaves the cannula cavity 40c, the donor tissue graft 60 is no longer constrained by the wall of the cannula 40 and can automatically unroll to a substantially planar configuration with the stroma side facing up.

Figure 19:
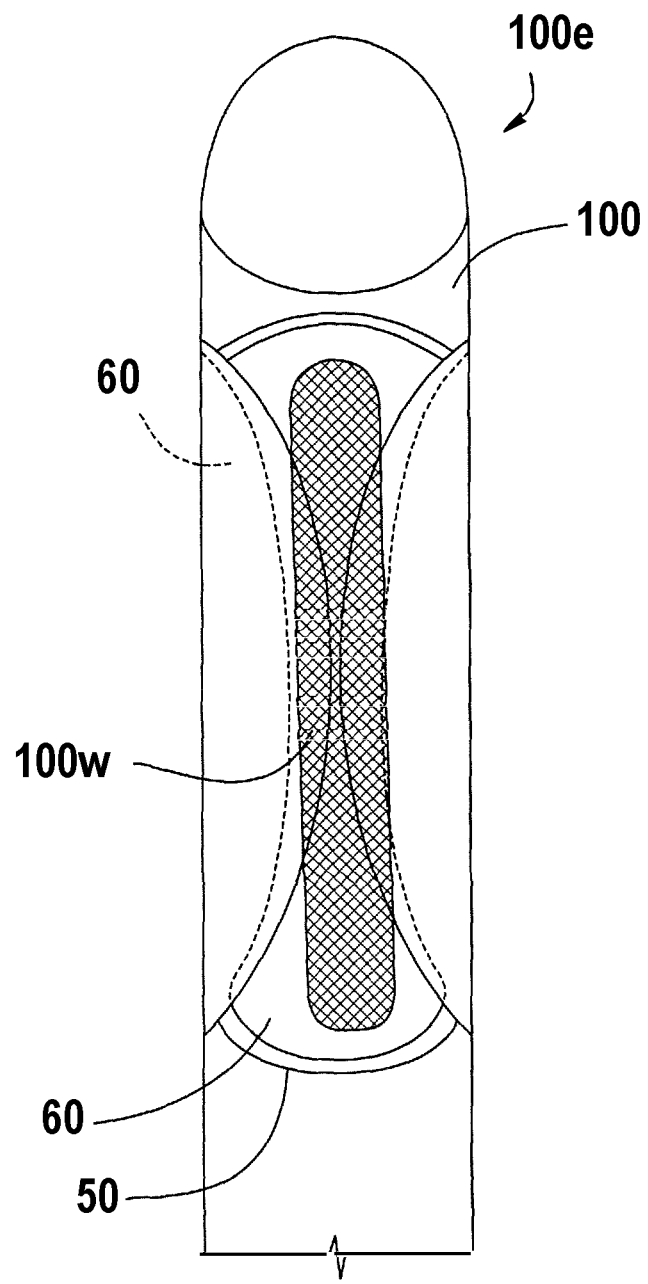
FIG. 19 is a schematic partial top view of a holding device configured to allow a user to view internal objects to visually confirm a desired orientation of the transplant tissue graft according to embodiments of the present disclosure.

FIG. 19 illustrates that the first cavity 40c can be configured to allow a user to view internal components to observe orientation of the graft and/or withdrawing, retracting, rolling and/or advancing action to visually confirm orientation of the donor tissue graft 60. The cannula 40 itself can be visually transmissiveor may include at least one viewing window. If the latter, there may be at least two viewing windows, spaced apart so that one resides above the other. As shown, a first viewing window 40w (illustrated by the cross-hatch markings) can axially extend over at least a major portion of the length of the donor tissue graft 60, typically a substantial length and with a width sufficient to allow a clinician to verify that the endothelial side is in position for implantation.

It is contemplated that rolling the donor tissue graft 60 can reduce damage to the donor endothelium over folded configurations and/or provide for smaller entry configurations. The donor tissue graft 60 can have a typical use diameter that is between about 8.0 mm to about 9.0 mm, typically between about 8.0 mm to about 8.25 mm; however, other suitable diameters may be used. The donor tissue disc 60 may also have a thickness that is typically between about 100-300 µm thick, and more typically between about 100-200 µm thick.

Figure 20:
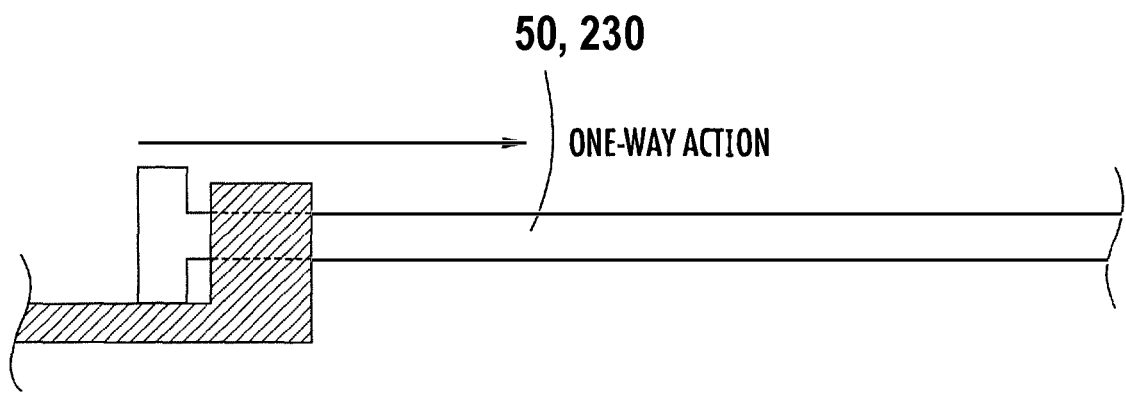
FIG. 20 is a schematic partial side view of a one-way action device according to other embodiments of the present disclosure.
Figure 21:
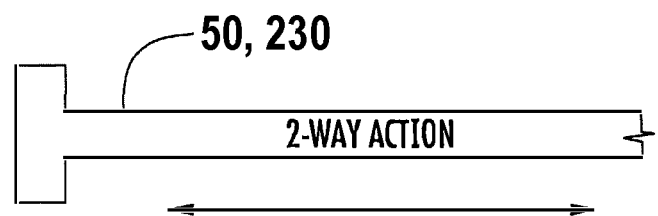
FIG. 21 is a schematic partial side view of a 2-way action device according to some embodiments of the present disclosure.

FIG. 20 illustrates that the support 50 and/or the deployment shaft 230 can operate with one-way action, while FIG. 21 illustrates that the support 50 and/or the deployment shaft 230 can be configured to operate with two-way action. Each may have a collar or other stop member that defines the stroke and/or directional travel.

The donor tissue graft disc 60 can be extracted from the donor eye in any suitable manner. Typically, for DSEK, the donor cornea is mounted within an artificial anterior chamber and pressurized. Manual dissection is used to remove the anterior corneal stroma. The dissected donor corneal tissue is then placed with the epithelial side down and trephination is carried out from the endothelial side using a disposable trephine. The diameter of the trephine matches the diameter of the circular mark placed on the corneal epithelium of the recipient cornea made at the beginning of the procedure. The donor disc is about 150 microns thick.

A small amount of viscoelastic is typically placed on the endothelial surface of the donor corneal disc. The donor corneal disc is then introduced into the anterior chamber using a taco-fold technique using forceps or inserted using a surgical glide or an inserter in its unfolded, or partially folded, state. Once within the anterior chamber, the donor disc is attached to the recipient's inner corneal stroma using a large air bubble. The donor/recipient interface is formed between donor and recipient corneal stroma. The donor disc is then centered to the recipient cornea using the pre-placed epithelial circular mark. About 10 minutes is allowed to elapse to facilitate initial donor recipient corneal disc adherence. The air bubble size may be decreased at the end of the procedure. The patient is asked to lay flat in the recovery room for about 45 minutes to an hour and also to lay flat for the most part during the first post-operative day.

For DSAEK, the donor corneal dissection is changed from a manual approach to an automated, microkeratome-assisted procedure. As a consequence, the stromal interface is improved in DSAEK as compared to DSEK. This improved donor-recipient interface is thought to contribute to improved quality of vision in DSAEK. For DSAEK, precut eye bank-prepared tissue is available. This eliminates the need for practitioner preparation of the donor corneal tissue in the operating room. However, practitioner preparation of donor tissue does allow for some degree of flexibility in the parameters of the donor tissue in the operating room.

The device 100 forms the donor tissue disc 60 so that the lower donor stromal surface is on the outside bottom surface of the rolled body 60c (FIG. 14).

To promote reliability, efficiency and/or ease in surgical placement, it is contemplated that a standard rolled orientation will be used and/or that different medical kits noting the practitioner's desired rolled orientation can be provided. The latter can allow a practitioner to order a kit that is suitable for the particular entry incision used (which may vary depending on patient eye structure) and/or for a desired unrolling technique (side to side, top to bottom, bottom to top, offset, and the like). The donor tissue rolled disc 60r may be configured for a temporal side or a superior entry. When unrolling in situ, rather than placing the rolled disc medially in the recipient stromal bed, the donor tissue rolled disc 60r may be inserted closer to a side edge portion of the eye, the side edge portion typically being the one that corresponds to the last rolled portion. The donor disc can then be unrolled in an opposite direction using physical or fluid forces.

To promote increased efficiency in surgical procedures, an OEM or medical company can provide the donor tissue graft 60 pre-formed in the rolled configuration and ready for surgery. The rolled donor tissue graft 60r may be held in a refrigerated storage condition prior to end use. The donor tissue disc 60 may be rolled using different end use disc sizes and provided in a preformed rolled configuration for different end use sizes (between about 8 mm to about 9 mm, including about 8.25 mm).

The cannula cavity 40c has a length L sufficient to hold the length of the donor tissue graft 60 therein, and is typically between about 8.5-10 mm long, typically about 9 mm long. As noted above, pressurized fluid can be introduced into the cannula cavity 40c to urge or force the rolled donor tissue graft 60r to exit the chamber. The fluid can comprise air, oxygen, saline, water or other suitable fluid. Where a lubricant and/or viscoelastic substance (such as HEALON from Pharmacia in Nutley, N.J.) is used to preserve or protect the rolled donor tissue graft 60r, a pre-delivery flushing may be desired to prepare the rolled donor tissue graft 60r for surgical insertion (to remove at least some of the substance from the rolled donor tissue graft 60r or cannula chamber 40c prior to placement in the body). The open-end 10e and donor tissue graft 60 may be enclosed with a reservoir 200, which is filled with a biocompatible fluid 250, and sealed with a reservoir cap 210 prior to use to help seal the disc in a sterile environment and/or placed in a sterile sealed package.

According to aspects of the present disclosure, a kit 350 can be provided with a device 100 in an empty configuration, with no donor tissue graft 60 loaded onto the flexible tissue support 50 or biocompatible fluid/liquid 250 loaded into the reservoir 200 or the fluid channel 220. The kit 350 can be opened under sterile conditions. If the reservoir base 160, reservoir 200 and reservoir cap 210 are attached to the device 100, they should be removed prior to loading donor tissue graft 60. Typically, the blocking guard 150 is not removed from the device 100 until the practitioner or other end user is ready to insert donor tissue 60 into the anterior chamber of the patient eye.

The fluid channel 220 can be flushed and primed with biocompatible liquid 250 by removing the fluid channel cap 170 and reversibly connecting a sterile pressurized fluid flow source to the fluid channel connector 190. Remove excess moisture from the support 50, e.g., with an absorbent sponge. Using aseptic technique, donor implant tissue 60 suitable for a small incision corneal transplant procedure (e.g., DLEK, DSEL, DSAEK) can be placed on the support 50, with donor tissue graft 60 previously prepared according to the requirements for each type of procedure as known in the art.

The donor tissue graft 60 can be set within the boundary of the visual alignment indicia 55 on the support 50. Larger diameter grafts will overhang the support 50 on the open side of the visual alignment indicia 55. Donor tissue 60 preferably does not extend past the front end of the support 50 or drape below the edge of the support 50. Once tissue is properly positioned on the support 50, remove excess moisture from around the donor tissue allograft 60 with, e.g., an absorbent sponge to enhance adherence of the donor tissue graft 60 to the support 50. During loading and deployment, a small amount of cohesive viscoelastic can be applied to the endothelium.

Rotating the retractor wheel 120 in the direction of the arrow causes the support 50 and donor tissue 60 to retracts and begins to roll, any overhanging donor tissue 60 edge can be tucked under the opposite edge. The practitioner loading the device 100 should carefully visualize the tissue loading until complete and, if necessary, repeat tucking any exposed edge. Donor tissue grafts 60 that do not overhang the carrier do not require tucking. For thinner donor tissue grafts 60, any overhanging donor tissue edges can be pre-tucked to avoid having the tissue drape over the side of the carrier. Continue rotating the retractor wheel 120 only in the direction indicated by the printed arrow until all retraction action stops. In some embodiments, the retractor wheel 120 will free spin once the support 50 and donor tissue graft 60 have been fully retracted into the cannula 40.

The combined reservoir 200 and reservoir base 160 (or separate reservoir 200 and reservoir base 160) can be attached to the deployment shaft distal end 180, and the reservoir can be filled with biocompatible fluid 250, either from a sterile pressurized fluid flow source reversibly attached to the fluid channel 220 by the fluid channel connector 190, or by filling the reservoir from the uncapped end. Once the device 100 has been loaded with donor tissue 60 and filled from fluid channel 220 to reservoir 200 with biocompatible fluid 250, the reservoir cap 210 and the fluid channel cap 170 are reattached. The device 100 is in a loaded configuration and can then be optionally mounted on tray 300 and sealed in a sterile package 310, or mounted directly in a sterile package 310 in the absence of a tray 100, to make a kit 350. The loaded kit 350 can be refrigerated and stored for future use in a small incision corneal transplant procedure (e.g., DLEK, DSEL, DSAEK). Kits 350 can be loaded and packaged at facilities that process donor tissue (e.g., eye banks). Loaded kits 350 can be shipped under tissue appropriate conditions to facilities that perform small incision corneal transplant procedures, enabling practitioners to avoid the time required to process donor tissue themselves.

The end user can open the loaded kit 350 and handle the device 100 using standard sterile procedures. Hold the device 100 by the body and remove the carrier tray 300 by gently pulling it down and away from the device 100. As before, the blocking guard 150 is typically not removed from the device 100 until ready to insert donor tissue graft 60 into the anterior chamber of the patient eye.

Once the practitioner is ready to perform the small incision procedure, he/she can roll the device 100 so that the deployment wheels 110 face up and firmly hold the deployment wheels 110 in position. They can then gently remove and discard the locking guard 150. Continue holding the deployment wheels 110 while inserting the beveled tip of the insertion sheath/cannula 40 through the small incision. The deployment wheels 110 must be held securely throughout the insertion process to avoid damage to donor tissue during insertion. Start and continue irrigation sourced from the sterile pressurized fluid flow source reversibly attached to the fluid channel connector 190 and delivered through the fluid channel to the cannula cavity 40c. If necessary, deepen the chamber by gently increasing fluid pressure while irrigation continues to flow. Continue irrigation as the insertion sheath/cannula 40 is moved across the anterior chamber past the far edge of the stripped stromal bed.

The donor tissue graft 60 can be deployed by rotating deployment wheels 110 forward towards the patient and rotating the device 100 45 degrees to the right, or clockwise, as viewed along the long axis of the device 100 from back to front as held by the practitioner. As the donor tissue graft 60 is exposed, roll the deployment wheels 110 until the donor tissue graft 60 is completely uncovered. The cannula sheath 40 will retract towards the incision during deployment. Hold the device in position as the donor tissue graft 60 deploys. After the allograft 60 has deployed, hold the deployment wheels 110 in their position and remove the device from the anterior chamber. An air bubble is placed to hold the donor tissue graft 60 in position. The device 100 may be discarded after use, but in certain embodiments they can recycled, or otherwise cleaned, sterilized and reused.

Embodiments include:

ZA. A donor corneal tissue storage and delivery device, comprising:
- a housing having a proximal end and a distal end;
- a cannula having a proximal end and a distal end, said cannula disposed at a distal end of the housing;
- a fluid channel connector disposed at a proximal end of the housing;
- at least one fluid channel with a proximal end and a distal end, the proximal end coupled to the fluid channel connector and the distal end disposed within the proximal end of the cannula;
- a flexible support configured to receive a donor corneal tissue and retract into the cannula;
- a retractor shaft coupled to the flexible support;
- one or more loading members held by the housing, coupled to the retractor shaft and operable to retract the retractor shaft and coupled flexible support thereby retracting the flexible support and donor corneal tissue into the cannula;
- a removable reservoir in fluid communication with the fluid channel and configured to enclose the flexible support and cannula and to receive a volume of fluid for hydrating the donor corneal tissue received by the flexible support while the flexible support is retracted into the cannula;
- a deployment shaft coupled to the cannula and configured to retract into the distal end of the housing; and
- one or more deployment members coupled to the deployment shaft and operable to cause the deployment shaft to retract the cannula and to deliver the donor corneal tissue to an implantation site from the flexible support retracted into the cannula.

ZB. The donor corneal tissue storage and delivery device according to embodiment ZA, wherein the cannula tapers toward the distal end of the housing.

ZC. The donor corneal tissue storage and delivery device according to either of embodiment ZA or ZB, wherein the one or more fluid channels is configured to receive fluid and direct the fluid to the cannula to provide irrigation to the donor corneal tissue and the implantation site.

ZD. The donor corneal tissue storage and delivery device according to either of embodiment ZA or ZB, wherein the one or more fluid channels is configured to receive fluid and direct the fluid to the cannula to provide irrigation to the donor corneal tissue and the implantation site and configured to flowably expel the donor corneal tissue when the one or more deployment members is operated.

ZE. The donor corneal tissue storage and delivery device according to any of embodiments ZA-ZC, further comprising a fluid pressure source configured to releasably engage the delivery device to allow a clinician to expel the corneal donor disc into a small incision scleral access site.

ZF. The donor corneal tissue storage and delivery device according to claim ZE, wherein the fluid pressure source is selected from the group consisting of syringe, hanging fluid bag, and infusion pump.

ZG. The donor corneal tissue storage and delivery device according to any of embodiments ZA-ZG, the cannula is sized to enter an incision less than about 4 mm in length.

ZH. The donor corneal tissue storage and delivery device according to any of embodiments ZA-ZG, wherein the fluid in the reservoir comprises a biocompatible fluid.

ZI. The donor corneal tissue storage and delivery device according to any of embodiments ZA-ZH, wherein at least a portion of the cannula is visually transmissive.

ZJ. The donor corneal tissue storage and delivery device according to any of embodiments ZA-ZI, wherein the cannula is slidably retractable relative to the housing, and wherein the device further comprises a locking guard member in communication with the one or more deployment members and configured to inhibit axial retraction of the cannula.

ZK. The donor corneal tissue storage and delivery device according to embodiment ZJ, wherein the one or more deployment members comprise one or more deployment wheels.

ZL. The donor corneal tissue storage and delivery device according to claim ZJ, wherein the locking guard member is removable from the housing to allow the one or more deployment members to engage the deployment shaft and to retract the cannula into the housing, wherein the one or more fluid channels remains stationary within the retracting cannula and acts to push the donor corneal tissue out of the cannula.

ZM. The donor corneal tissue storage and delivery device according to any of embodiments ZA-ZL, wherein the removable reservoir comprises a reservoir base coupled to the distal end of the deployment shaft, a reservoir body removably coupled to the reservoir base, and a reservoir cap removably coupled to the reservoir body.

ZN. The donor corneal tissue storage and delivery device according to any of embodiments ZA-ZM, wherein the reservoir base is removably coupled to the distal end of the deployment shaft.

ZO. The donor corneal tissue storage and delivery device according to any of embodiments ZA-ZN, wherein the flexible support and donor corneal tissue adopt a rolled shape when retracted into the cannula.

ZP. A donor corneal tissue storage and delivery device kit, comprising:
a sterile package; and
a donor corneal tissue storage and delivery device in the sterile package,
wherein the donor corneal tissue storage and delivery device comprises:
a housing having a proximal end and a distal end;
a cannula having a proximal end and a distal end, said cannula disposed at a distal end of the housing;
a fluid channel connector disposed at a proximal end of the housing;
at least one fluid channel with a proximal end and a distal end, the proximal end coupled to the fluid channel connector and the distal end disposed within the proximal end of the cannula;
a flexible support configured to receive a donor corneal tissue and retract into the cannula;
a retractor shaft coupled to the flexible support;
one or more loading members held by the housing, coupled to the retractor shaft and operable to retract the retractor shaft and coupled flexible support thereby retracting the flexible support and donor corneal tissue into the cannula;
a removable reservoir in fluid communication with the fluid channel and configured to enclose the flexible support and cannula and to receive a volume of fluid for hydrating the donor corneal tissue received by the flexible support while the flexible support is retracted into the cannula;
a deployment shaft coupled to the cannula and configured to retract into the distal end of the housing; and
one or more deployment members coupled to the deployment shaft and operable to cause the deployment shaft to retract the cannula and to deliver the donor corneal tissue to an implantation site from the flexible support retracted into the cannula.

A. A donor corneal tissue storage and delivery device kit, comprising:
a sterile package; and
a delivery device holding donor corneal tissue in the sterile package,
wherein the delivery device comprises:
a housing with at least one fluid channel therein the at least one fluid channel comprising a proximal end and a distal end, the proximal end coupled to a fluid channel connector and the distal end residing proximate to or within a rearward end portion of a cannula;
a flexible support holding the donor corneal tissue each having a rolled shape while retracted inside the cannula;
a removable reservoir in fluid communication with the fluid channel configured to leaklessly hold a volume of fluid to submerge the donor corneal tissue while the tissue resides on the flexible support retracted into the cannula; and
one or more deployment members held by the housing and operably attached to a deployment shaft that is in communication with the cannula to retract the cannula and deliver the donor corneal tissue into a target implantation site.

B. A donor corneal tissue storage and delivery device kit according to embodiment A, wherein the cannula has a tapered forward edge portion.

C. A donor corneal tissue storage and delivery device kit according to any of embodiments A-B, wherein the delivery device is configured to cooperate with pressurized fluid to expel the rolled donor corneal tissue from the holding chamber into position at the target implantation site.

D. A donor corneal tissue storage and delivery device kit according to any of embodiments A-C, further comprising a fluid pressure source configured to releasably engage the delivery device to allow a clinician to expel the corneal donor disc into a small incision scleral access site.

E. A donor corneal tissue storage and delivery device kit according to any of embodiments A-D, wherein once the reservoir is removed, a forward end portion of the cannula is sized and configured to enter a scleral access incision sized at less than about 4 mm.

F. A donor corneal tissue storage and delivery device kit according to any of embodiments A-E, wherein the fluid in the reservoir comprises a biocompatible fluid.

G. A donor corneal tissue storage and delivery device kit according to embodiment F, wherein the biocompatible fluid is selected from the group consisting of cornea storage solution, Optisol, Optisol GS, Dexsol, McCarey-Kaufman Media, Life 4° C. solution, sterile water, saline, and viscoelastic material.

H. A donor corneal tissue storage and delivery device kit according to any of embodiments A-G, wherein the delivery device has a forward end portion that is axially spaced apart from and opposing the rearward end portion, wherein the forward end portion comprises the cannula, and wherein the rearward end portion comprises fluid channel connector sized and configured to matably receive a fluid pressure source.

I. The donor corneal tissue storage and delivery device kit according to embodiment H, wherein the fluid pressure source is selected from the group consisting of syringe, hanging fluid bag, and infusion pump.

J. A donor corneal tissue storage and delivery device kit according to any of embodiments A-I, wherein at least a portion of the cannula is visually transmissive.

K. A donor corneal tissue storage and delivery device kit according to any of embodiments A-J, wherein the cannula is slidably retractable relative to the housing, and wherein the device further comprises a locking guard member in communication with the deployment member configured to inhibit inadvertent axial retraction of the cannula beyond a first hold location.

L. A donor corneal tissue storage and delivery device kit according to any of embodiments A-K, wherein the deployment member comprises one or more deployment wheels.

M. A donor corneal tissue storage and delivery device kit according to embodiment K, wherein when the locking guard member is removed and the deployment member engages the deployment shaft thereby retracting the cannula into the body of the housing, the distal end of the fluid channel remains stationary within the retracting cannula and acts to push the donor corneal tissue out of the cannula.

N. A donor corneal tissue storage and delivery device kit according to any of embodiments A-M, wherein the removable reservoir is partially removeable.

O. A donor corneal tissue storage and delivery device kit according to any of embodiments A-N, wherein the removable reservoir is completely removeable, including reservoir base, body and cap.

P. A donor corneal tissue loading device kit, comprising:
a sterile package; and
a loading device empty of but prepared for holding donor corneal tissue in the sterile package,
wherein the loading device comprises:
a housing with at least one fluid channel therein, the at least one fluid channel comprising a proximal end and a distal end, the proximal end coupled to a fluid channel connector and the distal end residing proximate to or within a rearward end portion of a cannula;
a flexible support free from donor corneal tissue and extending outside the cannula, wherein the flexible support is configured to slidably retract into the cannula while holding donor corneal tissue, wherein the flexible support has a planar shape outside the cannula, and wherein the flexible support and the donor corneal tissue, once loaded thereon, have a rolled shape inside the cannula;
an empty removable reservoir in fluid communication with the fluid channel configured to leaklessly hold a volume of fluid to submerge donor corneal tissue after the tissue is placed on the flexible support and retracted into the cannula;
one or more loading members held by the housing and operably attached to a retractor shaft that is in communication with the flexible support to retract the flexible support and donor corneal tissue into the cannula; and
one or more deployment members held by the housing and operably attached to a deployment shaft that is in communication with the cannula to retract the cannula and deliver the donor corneal tissue into a target implantation site.

Q. A donor corneal tissue loading device kit according to embodiment P, further comprising a fluid pressure source configured to releasably engage the loading device to allow a clinician or device operator to fill the fluid channel and reservoir with a fluid.

R. The donor corneal tissue loading device kit according to embodiment Q, wherein the fluid pressure source is selected from the group consisting of syringe, hanging fluid bag, and infusion pump.

S. A donor corneal tissue loading device kit according to any of embodiments P-R, wherein when a fluid is added to the reservoir, the fluid comprises a biocompatible fluid.

T. A donor corneal tissue loading device kit according to embodiment S, wherein the biocompatible fluid is selected from the group consisting of cornea storage solution, Optisol, Optisol GS, Dexsol, McCarey-Kaufman Media, Life 4° C. solution, sterile water, saline, and viscoelastic material.

U. A donor corneal tissue loading device kit according to any of embodiments P-T, wherein the cannula has a tapered forward edge portion.

V. A donor corneal tissue loading device kit according to any of embodiments P-U, wherein a forward end portion of the cannula is sized and configured to enter a scleral access incision sized at less than about 4 mm.

W. A donor corneal tissue loading device kit according to any of embodiments P-V, wherein at least a portion of the cannula is visually transmissive.

X. A donor corneal tissue loading device kit according to any of embodiments P-W, wherein the flexible support is in operable communication with a retractor shaft, which shaft is slidably retractable relative to the housing, and wherein the surgical kit further comprises a locking guard member in communication with the deployment member configured to inhibit inadvertent axial retraction of the cannula beyond a first hold location.

Y. A donor corneal tissue loading device kit according to any of embodiments P-W, wherein the loading member comprises one or more retractor wheels.

Z. A donor corneal tissue loading device kit according to any of embodiments P-X, wherein the empty removable reservoir is assembled onto the loading device in the kit.

AA. A donor corneal tissue loading device kit according to any of embodiments P-Y, wherein the empty removable reservoir is disassembled in the kit.

AB. A donor corneal tissue storage and delivery device, comprising:
a housing with at least one fluid channel therein, the at least one fluid channel comprising a proximal end and a distal end, the proximal end coupled to a fluid channel connector and the distal end residing proximate to or within a rearward end portion of a cannula;
a flexible support holding the donor corneal tissue each having a rolled shape while retracted inside the cannula;
a removable reservoir in fluid communication with the fluid channel configured to leaklessly hold a volume of fluid to submerge the donor corneal tissue while the tissue resides on the flexible support retracted into the cannula; and
one or more deployment members held by the housing and operably attached to a deployment shaft that is in communication with the cannula to retract the cannula and deliver the donor corneal tissue into a target implantation site.

AC. A donor corneal tissue storage and delivery device according to embodiment AB, wherein the cannula has a tapered forward edge portion.

AD. A donor corneal tissue storage and delivery device according to any of embodiments AB-AC, wherein the delivery device is configured to cooperate with pressurized fluid to expel the rolled donor corneal tissue from the holding chamber into position at the target implantation site.

AE. A donor corneal tissue storage and delivery device according to embodiment AD, further comprising a fluid pressure source configured to releasably engage the delivery device to allow a clinician to expel the corneal donor disc into a small incision scleral access site.

AF. A donor corneal tissue storage and delivery device according to any of embodiments AB-AE, wherein once the reservoir is removed, a forward end portion of the cannula is sized and configured to enter a scleral access incision sized at less than about 4 mm.

AG. A donor corneal tissue storage and delivery device according to any of embodiments AB-AF, wherein the fluid in the reservoir comprises a biocompatible fluid.

AH. A donor corneal tissue storage and delivery device according to embodiment AG, wherein the biocompatible fluid is selected from the group consisting of cornea storage solution, Optisol, Optisol GS, Dexsol, McCarey-Kaufman Media, Life 4° C. solution, sterile water, saline, and viscoelastic material.

AI. A donor corneal tissue storage and delivery device according to any of embodiments AB-AH, wherein the delivery device has a forward end portion that is axially spaced apart from and opposing the rearward end portion, wherein the forward end portion comprises the cannula, and wherein the rearward end portion comprises fluid channel connector sized and configured to matably receive a fluid pressure source.

AJ. The donor corneal tissue storage and delivery device according to embodiment AI, wherein the fluid pressure source is selected from the group consisting of syringe, hanging fluid bag, and infusion pump.

AK. A donor corneal tissue storage and delivery device according to any of embodiments AB-AJ, wherein at least a portion of the cannula is visually transmissive.

AL. A donor corneal tissue storage and delivery device according to any of embodiments AB-AK, wherein the cannula is slidably retractable relative to the housing, and wherein the device further comprises a locking guard member in communication with the deployment member configured to inhibit inadvertent axial retraction of the cannula beyond a first hold location.

AM. A donor corneal tissue storage and delivery device according to embodiment AL, wherein the deployment member comprises one or more deployment wheels.

AN. A donor corneal tissue storage and delivery device according to embodiment AL, wherein when the locking guard member is removed and the deployment member engages the deployment shaft thereby retracting the cannula into the body of the housing, the distal end of the fluid channel remains stationary within the retracting cannula and acts to push the donor corneal tissue out of the cannula.

AO. A donor corneal tissue storage and delivery device according to any of embodiments AB-AN, wherein the removable reservoir is partially removeable.

AP. A donor corneal tissue storage and delivery device according to any of embodiments AB-AO, wherein the removable reservoir is completely removeable, including reservoir base, body and cap.

AQ. A donor corneal tissue loading device, comprising:
a housing with at least one fluid channel therein, the at least one fluid channel comprising a proximal end and a distal end, the proximal end coupled to a fluid channel connector and the distal end residing proximate to or within a rearward end portion of a cannula;
a flexible support free from donor corneal tissue and extending outside the cannula, wherein the flexible support is configured to slidably retract into the cannula while holding donor corneal tissue, wherein the flexible support has a planar shape outside the cannula, and wherein the flexible support and the donor corneal tissue, once loaded thereon, have a rolled shape inside the cannula;
an empty removable reservoir in fluid communication with the fluid channel configured to leaklessly hold a volume of fluid to submerge donor corneal tissue after the tissue is placed on the flexible support and retracted into the cannula;
one or more loading members held by the housing and operably attached to a retractor shaft that is in communication with the flexible support to retract the flexible support and donor corneal tissue into the cannula; and
one or more deployment members held by the housing and operably attached to a deployment shaft that is in communication with the cannula to retract the cannula and deliver the donor corneal tissue into a target implantation site.

AR. A donor corneal tissue loading device according to embodiment AQ, further comprising a fluid pressure source configured to releasably engage the loading device to allow a clinician or device operator to fill the fluid channel and reservoir with a fluid.

AS. The donor corneal tissue loading device according to embodiment AR, wherein the fluid pressure source is selected from the group consisting of syringe, hanging fluid bag, and infusion pump.

AT. A donor corneal tissue loading device according to any of embodiments AQ-AS, wherein when a fluid is added to the reservoir, the fluid comprises a biocompatible fluid.

AU. A donor corneal tissue loading device according to embodiment AT, wherein the biocompatible fluid is selected from the group consisting of cornea storage solution, Optisol, Optisol GS, Dexsol, McCarey-Kaufman Media, Life 4° C. solution, sterile water, saline, and viscoelastic material.

AV. A donor corneal tissue loading device according to any of embodiments AQ-AU, wherein the cannula has a tapered forward edge portion.

AW. A donor corneal tissue loading device according to any of embodiments AQ-AV, wherein a forward end portion of the cannula is sized and configured to enter a scleral access incision sized at less than about 4 mm.

AX. A donor corneal tissue loading device according to any of embodiments AQ-AW, wherein at least a portion of the cannula is visually transmissive.

AY. A donor corneal tissue loading device according to any of embodiments AQ-AX, wherein the flexible support is in communication with a retractor shaft slidably retractable relative to the housing, and wherein the surgical kit further comprises a locking guard member in communication with the deployment member configured to inhibit inadvertent axial retraction of the cannula beyond a first hold location.

AZ. A donor corneal tissue loading device according to any of embodiments AQ-AY, wherein the loading member comprises one or more retractor wheels.

BA. A donor corneal tissue loading device according to any of embodiments AQ-AZ, wherein the empty removable reservoir is preassembled onto the loading device.

BB. A donor corneal tissue loading device according to any of embodiments AQ-BA, wherein the empty removable reservoir is provided unassembled.

As described above, like numbers refer to like elements throughout. In the figures, the thickness of certain lines, layers, components, elements or features may be exaggerated for clarity. Broken lines illustrate optional features or operations unless specified otherwise. Features described or shown with respect to one embodiment may be used with a different embodiment.

BC. A donor corneal tissue storage and delivery device kit according to any of embodiments A-O, wherein the donor corneal tissue is suitable for a small incision, partial thickness corneal replacement procedure.

BD. A donor corneal tissue storage and delivery device kit according to embodiment BC, wherein the partial thickness corneal replacement procedure is selected from the group consisting of deep lamellar endothelial keratoplasty (DLEK), Descemet's stripping endothelial keratoplasty (DSEK) and Descemet's stripping automated endothelial keratoplasty (DSAEK).

BE. A donor corneal tissue loading device kit according to any of embodiments P-AA, wherein the donor corneal tissue is suitable for a small incision, partial thickness corneal replacement procedure.

BF. A donor corneal tissue storage and delivery device kit according to embodiment BE, wherein the partial thickness corneal replacement procedure is selected from the group consisting of deep lamellar endothelial keratoplasty (DLEK), Descemet's stripping endothelial keratoplasty (DSEK) and Descemet's stripping automated endothelial keratoplasty (DSAEK).

BG. A donor corneal tissue storage and delivery device according to any of embodiments AB-AP, wherein the donor corneal tissue is suitable for a small incision, partial thickness corneal replacement procedure.

BH. A donor corneal tissue storage and delivery device according to embodiment BG, wherein the partial thickness corneal replacement procedure is selected from the group consisting of deep lamellar endothelial keratoplasty (DLEK), Descemet's stripping endothelial keratoplasty (DSEK) and Descemet's stripping automated endothelial keratoplasty (DSAEK).

BI. A donor corneal tissue loading device according to any of embodiments AQ-BB, wherein the donor corneal tissue is suitable for a small incision, partial thickness corneal replacement procedure.

BJ. A donor corneal tissue storage and delivery device kit according to embodiment BI, wherein the partial thickness corneal replacement procedure is selected from the group consisting of deep lamellar endothelial keratoplasty (DLEK), Descemet's stripping endothelial keratoplasty (DSEK) and Descemet's stripping automated endothelial keratoplasty (DSAEK).

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y" As used herein, phrases such as "from about X to Y" mean "from about X to about Y"

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present disclosure. The sequence of operations (or steps) is not limited to the order presented in the claims or figures unless specifically indicated otherwise.

The term "rolled", and derivatives thereof, refer to turning or coiling the donor tissue about an axis into a substantially rolled configuration, thus inhibiting the formation of sharp fold edges. The terms "small opening" or "small incision" means an opening that is less than about 5 mm wide and/or long, typically about 3 mm. The term "compact configuration" means that the donor disc is configured smaller than its end use configuration by at least about 40%, typically less than about 50%. For example, if the end use configuration is about an 8.25 mm diameter or width, then the compact configuration can provide a width that about or less than about 5 mm, typically about or less than 4 mm. In some configurations, the compact configuration can be about 60% less than the use or normal width, such as about 3 mm or less, and may be about 2.5 mm.

The foregoing is illustrative and is not to be construed as limiting thereof. Although a few exemplary embodiments have been described, those skilled in the art will readily appreciate that many modifications are possible in the exemplary embodiments without materially departing from the novel teachings and advantages. Accordingly, all such modifications are intended to be included within the scope of the present disclosure.

What is claimed is:

1. A donor corneal tissue storage and delivery device, comprising:
   a storage fluid;
   a housing having a proximal end and a distal end;
   a cannula having a proximal end and a distal end, said cannula disposed at a distal end of the housing;
   a fluid channel connector disposed at a proximal end of the housing;
   at least one fluid channel with a proximal end and a distal end, the proximal end coupled to the fluid channel connector and the distal end disposed within the proximal end of the cannula;
   a flexible support configured to receive a donor corneal tissue and retract into the cannula;
   a retractor shaft coupled to the flexible support;
   one or more loading members held by the housing, coupled to the retractor shaft and operable to retract the retractor shaft and coupled flexible support thereby retracting the flexible support and donor corneal tissue into the cannula;
   a deployment shaft coupled to the cannula and configured to retract into the distal end of the housing;
   one or more deployment members coupled to the deployment shaft and operable to cause the deployment shaft to retract the cannula and to deliver the donor corneal tissue to an implantation site from the flexible support retracted into the cannula;
   a removable reservoir comprising a reservoir base configured to removably couple the removable reservoir to a distal end of the deployment shaft, wherein the removable reservoir is in fluid communication with the at least one fluid channel and encloses the flexible support and cannula when the removable reservoir is removably coupled to the distal end of the deployment shaft, wherein the removable reservoir is configured to receive the storage fluid for hydrating the donor corneal tissue received by the flexible support while the flexible support is retracted into the cannula; and
   wherein the at least one fluid channel, cannula, and the removable reservoir are all filled with the storage fluid.

2. The donor corneal tissue storage and delivery device according to claim 1, wherein the cannula tapers toward the distal end of the housing.

3. The donor corneal tissue storage and delivery device according to claim 1, wherein the cannula is slidably retractable relative to the housing, and wherein the device further comprises a locking guard member in communication with the one or more deployment members and configured to inhibit axial retraction of the cannula.

4. The donor corneal tissue storage and delivery device according to claim 3, wherein the locking guard member is removable from the housing to allow the one or more deployment members to engage the deployment shaft and to retract the cannula into the housing, wherein the at least one fluid channel remains stationary within the retracting cannula and acts to push the donor corneal tissue out of the cannula.

5. The donor corneal tissue storage and delivery device according to claim 3, wherein the one or more deployment members comprise one or more deployment wheels.

6. The donor corneal tissue storage and delivery device according to claim 1, wherein the at least one fluid channel is configured to receive irrigation fluid and direct the irrigation fluid to the cannula to provide irrigation to the donor corneal tissue and the implantation site.

7. The donor corneal tissue storage and delivery device according to claim 6, further comprising a fluid pressure source configured to releasably engage the fluid channel connector to help deliver the donor corneal tissue into a small incision scleral access site.

8. The donor corneal tissue storage and delivery device according to claim 7, wherein the fluid pressure source is selected from the group consisting of syringe, hanging fluid bag, and infusion pump.

9. The donor corneal tissue storage and delivery device according to claim 1, wherein the at least one fluid channel is configured to receive irrigation fluid and direct the irrigation fluid to the cannula to provide irrigation to the donor corneal tissue and the implantation site and configured to help flowably deliver the donor corneal tissue when the one or more deployment members is operated.

10. The donor corneal tissue storage and delivery device according to claim 1, the cannula is sized to enter an incision less than about 4 mm in length.

11. The donor corneal tissue storage and delivery device according to claim 1, wherein the removable reservoir contains the storage fluid, wherein the storage fluid comprises a biocompatible fluid.

12. The donor corneal tissue storage and delivery device according to claim 11, wherein the biocompatible fluid is a cornea storage solution.

13. The donor corneal tissue storage and delivery device according to claim 1, wherein at least a portion of the cannula is visually transmissive.

14. The donor corneal tissue storage and delivery device according to claim 1, wherein the removable reservoir further comprises a reservoir body extending distally from the reservoir base and a reservoir cap distal the reservoir base, the reservoir cap removably coupled to the reservoir body.

15. The donor corneal tissue storage and delivery device according to claim 1, wherein the reservoir base is removably coupled to the distal end of the deployment shaft.

16. The donor corneal tissue storage and delivery device according to claim 1, wherein the flexible support and donor corneal tissue adopt a rolled shape when retracted into the cannula.

17. The donor corneal tissue storage and delivery device according to claim 1, wherein the removable reservoir further comprises a fluid flow restrictor disposed therein.

18. The donor corneal tissue storage and delivery device according to claim 1, wherein a proximal portion of the deployment shaft and the retractor shaft are slidably engaged at a junction, the junction including a one-way valve or gasket that inhibits leakage of the storage fluid.

19. A donor corneal tissue storage and delivery device kit, comprising:
   a sterile package; and
   a donor corneal tissue storage and delivery device in the sterile package,
   wherein the donor corneal tissue storage and delivery device comprises:
   a storage fluid;
   a housing having a proximal end and a distal end;
   a cannula having a proximal end and a distal end, said cannula disposed at a distal end of the housing;
   a fluid channel connector disposed at a proximal end of the housing;

at least one fluid channel with a proximal end and a distal end, the proximal end coupled to the fluid channel connector and the distal end disposed within the proximal end of the cannula;

a flexible support configured to receive a donor corneal tissue and retract into the cannula;

a retractor shaft coupled to the flexible support;

one or more loading members held by the housing, coupled to the retractor shaft and operable to retract the retractor shaft and coupled flexible support thereby retracting the flexible support and donor corneal tissue into the cannula;

a deployment shaft coupled to the cannula and configured to retract into the distal end of the housing;

one or more deployment members coupled to the deployment shaft and operable to cause the deployment shaft to retract the cannula and to deliver the donor corneal tissue to an implantation site from the flexible support retracted into the cannula;

a removable reservoir comprising a reservoir base configured to removably couple the removable reservoir to a distal end of the deployment shaft, wherein the removable reservoir is in fluid communication with the at least one fluid channel and encloses the flexible support and cannula when the removable reservoir is removably coupled to the distal end of the deployment shaft, wherein the removable reservoir is configured to receive the storage fluid for hydrating the donor corneal tissue received by the flexible support while the flexible support is retracted into the cannula; and wherein the at least one fluid channel, cannula, and the removable reservoir are all filled with the storage fluid.

20. The donor corneal tissue storage and delivery device kit of claim 19, wherein the removable reservoir contains the storage fluid, wherein the storage fluid comprises a cornea storage solution.

21. The donor corneal tissue storage and delivery device kit of claim 19, wherein the removable reservoir further comprises a reservoir body extending distally from the reservoir base and a reservoir cap distal the reservoir base, the reservoir cap removably coupled to the reservoir body.

22. The donor corneal tissue storage and delivery device kit of claim 19, wherein the removable reservoir further comprises a fluid flow restrictor disposed therein.

23. The donor corneal tissue storage and delivery device kit of claim 19, wherein a proximal portion of the deployment shaft and the retractor shaft are slidably engaged at a junction, the junction including a one-way valve or gasket that inhibits leakage of the storage fluid.

* * * * *